United States Patent
Frederick et al.

(10) Patent No.: US 9,504,577 B2
(45) Date of Patent: *Nov. 29, 2016

(54) METHODS AND APPARATUS FOR FAI SURGERIES

(71) Applicant: Smith & Nephew, Inc., Memphis, TN (US)

(72) Inventors: Phillip Frederick, Memphis, TN (US);
Kevin Belew, Hernando, MS (US);
Lauren Jasper, Memphis, TN (US);
James Gatewood, Memphis, TN (US);
Luke Gibson, Southaven, MS (US);
John Masonis, Charlotte, NC (US);
Michael Cooper, Nesbit, MS (US);
David C. Kelman, Collierville, TN (US)

(73) Assignee: Smith & Nephew, Inc., Cordova, TN (US)

( * ) Notice: Subject to any disclaimer, the term of this patent is extended or adjusted under 35 U.S.C. 154(b) by 37 days.

This patent is subject to a terminal disclaimer.

(21) Appl. No.: 14/534,751

(22) Filed: Nov. 6, 2014

(65) Prior Publication Data

US 2015/0066151 A1 Mar. 5, 2015

Related U.S. Application Data

(63) Continuation of application No. 13/202,612, filed as application No. PCT/US2010/025292 on Feb. 25, 2010, now Pat. No. 8,900,320.

(60) Provisional application No. 61/155,060, filed on Feb. 24, 2009.

(51) Int. Cl.
*A61F 2/34* (2006.01)
*A61F 2/30* (2006.01)
(Continued)

(52) U.S. Cl.
CPC ............ *A61F 2/30728* (2013.01); *A61F 2/32* (2013.01); *A61F 2/34* (2013.01); *A61F 2/4657* (2013.01);
(Continued)

(58) Field of Classification Search
CPC .... A61F 2/34; A61F 2/3872; A61F 2/30756; A61F 2002/3401; A61F 2002/3424; A61F 2002/343; A61F 2002/3432; A61F 2002/3466; A61F 2002/30764
See application file for complete search history.

(56) References Cited

U.S. PATENT DOCUMENTS

| 2,691,979 A | 10/1954 | Watson |
| 3,740,769 A | 6/1973 | Haboush |

(Continued)

FOREIGN PATENT DOCUMENTS

| AU | 2006334522 A1 | 7/2007 |
| AU | 2008260279 A1 | 12/2008 |

(Continued)

OTHER PUBLICATIONS

Chinese Search Report; State Intellectual Property Office of People's Republic of China; Chinese Patent Application No. 201080017951.X; Jan. 4, 2015; 5 pages.

(Continued)

*Primary Examiner* — Alvin Stewart
(74) *Attorney, Agent, or Firm* — Taft Stettinius & Hollister LLP

(57) ABSTRACT

A partial rim implant for an acetabulum in a pelvic bone comprises a ridge, a bearing surface, and a fixation surface. The ridge is oriented to replace a labrum. The bearing surface is configured to align with the articulating surface of the acetabulum. The bearing surface extends from the ridge toward the apex of the acetabulum. The fixation surface is configured to fix the implant to a prepared bone surface of the pelvic bone.

20 Claims, 21 Drawing Sheets

(51) Int. Cl.
*A61F 2/46* (2006.01)
*A61F 2/32* (2006.01)
*A61B 17/04* (2006.01)
*A61B 17/17* (2006.01)
*A61B 17/84* (2006.01)
*A61B 17/86* (2006.01)
*A61B 17/02* (2006.01)

(52) U.S. Cl.
CPC ........ *A61B 17/0469* (2013.01); *A61B 17/1746* (2013.01); *A61B 17/842* (2013.01); *A61B 17/86* (2013.01); *A61B 2017/0275* (2013.01); *A61F 2002/30014* (2013.01); *A61F 2002/3085* (2013.01); *A61F 2002/30131* (2013.01); *A61F 2002/30192* (2013.01); *A61F 2002/30461* (2013.01); *A61F 2002/30576* (2013.01); *A61F 2002/30578* (2013.01); *A61F 2002/30731* (2013.01); *A61F 2002/30736* (2013.01); *A61F 2002/3432* (2013.01); *A61F 2002/3487* (2013.01); *A61F 2002/4658* (2013.01); *A61F 2220/0075* (2013.01); *A61F 2230/0013* (2013.01); *A61F 2230/0041* (2013.01); *A61F 2250/0018* (2013.01)

(56) References Cited

U.S. PATENT DOCUMENTS

| | | | |
|---|---|---|---|
| 4,502,161 A | 3/1985 | Wall | |
| 4,851,006 A | 7/1989 | Tuke | |
| 4,919,667 A | 4/1990 | Richmond | |
| 4,919,672 A | 4/1990 | Millar et al. | |
| 4,955,919 A | 9/1990 | Pappas et al. | |
| 4,959,072 A | 9/1990 | Morscher et al. | |
| 5,047,062 A | 9/1991 | Pappas et al. | |
| 5,067,964 A | 11/1991 | Richmond et al. | |
| 5,127,920 A | 7/1992 | MacArthur | |
| 5,133,764 A | 7/1992 | Pappas et al. | |
| 5,176,711 A | 1/1993 | Grimes | |
| 5,197,989 A | 3/1993 | Hinckfuss et al. | |
| 5,376,122 A | 12/1994 | Pappas et al. | |
| 5,376,125 A | 12/1994 | Winkler et al. | |
| 5,609,646 A | 3/1997 | Field et al. | |
| 5,735,900 A | 4/1998 | Barrett et al. | |
| 5,766,262 A | 6/1998 | Mikhail | |
| 5,871,548 A | 2/1999 | Sanders et al. | |
| 5,879,404 A | 3/1999 | Bateman et al. | |
| 5,880,976 A | 3/1999 | DiGioia III et al. | |
| 5,913,899 A | 6/1999 | Barrett et al. | |
| 5,995,738 A | 11/1999 | DiGioia et al. | |
| 6,002,859 A | 12/1999 | DiGioia, III et al. | |
| 6,004,353 A | 12/1999 | Masini | |
| 6,056,777 A | 5/2000 | McDowell | |
| 6,120,546 A | 9/2000 | Dye et al. | |
| 6,136,034 A | 10/2000 | Townley | |
| 6,162,257 A | 12/2000 | Gustilo et al. | |
| 6,171,340 B1 | 1/2001 | McDowell | |
| 6,200,350 B1 | 3/2001 | Masini | |
| 6,205,411 B1 | 3/2001 | DiGioia, III et al. | |
| 6,299,647 B1 | 10/2001 | Townley | |
| 6,306,173 B1 | 10/2001 | Masini | |
| 6,383,224 B1 | 5/2002 | Gie et al. | |
| 6,383,225 B2 | 5/2002 | Masini | |
| 6,416,553 B1 | 7/2002 | White et al. | |
| 6,475,243 B1 | 11/2002 | Sheldon et al. | |
| 6,695,883 B2 | 2/2004 | Crofford | |
| 6,758,864 B2 | 7/2004 | Storer et al. | |
| 6,783,553 B2 | 8/2004 | Grimes | |
| 6,908,486 B2 | 6/2005 | Lewallen | |
| 6,923,833 B2 | 8/2005 | Wasielewski | |
| 7,022,142 B2 | 4/2006 | Johnson | |
| 7,060,102 B2 | 6/2006 | Thompson et al. | |
| 7,074,241 B2 | 7/2006 | McKinnon | |
| 7,104,995 B2 | 9/2006 | Crofford | |
| 7,115,145 B2 | 10/2006 | Richards | |
| 7,169,186 B2 | 1/2007 | Harris et al. | |
| 7,291,176 B2 | 11/2007 | Serra et al. | |
| 7,476,254 B2 | 1/2009 | White et al. | |
| 7,611,541 B2 | 11/2009 | Thompson et al. | |
| 7,615,083 B2 | 11/2009 | Wasielewski | |
| 7,682,398 B2 | 3/2010 | Croxton et al. | |
| 7,695,474 B2 | 4/2010 | Crofford | |
| 7,708,783 B2 | 5/2010 | Richards | |
| 7,722,678 B2 | 5/2010 | Brown et al. | |
| 7,758,643 B2 | 7/2010 | Stone et al. | |
| 7,819,918 B2 | 10/2010 | Malaviya et al. | |
| 8,021,432 B2 | 9/2011 | Meridew et al. | |
| 8,048,166 B2 | 11/2011 | Brown et al. | |
| 8,118,868 B2 | 2/2012 | May et al. | |
| 8,292,967 B2 | 10/2012 | Brown et al. | |
| 8,403,985 B2 | 3/2013 | Hodorek | |
| 8,900,320 B2 * | 12/2014 | Frederick ................. A61F 2/32 623/22.32 | |
| 2001/0001121 A1 | 5/2001 | Lombardo et al. | |
| 2002/0128653 A1 | 9/2002 | Haidukewych | |
| 2002/0128720 A1 | 9/2002 | Masini | |
| 2003/0187513 A1 | 10/2003 | Durniak | |
| 2003/0212458 A1 | 11/2003 | Harris et al. | |
| 2003/0212459 A1 | 11/2003 | Gibbs | |
| 2004/0059416 A1 | 3/2004 | Murray et al. | |
| 2004/0083004 A1 | 4/2004 | Wasielewski | |
| 2004/0133979 A1 | 7/2004 | Newkirk et al. | |
| 2004/0138757 A1 | 7/2004 | Nadzadi et al. | |
| 2004/0153062 A1 | 8/2004 | McGinley et al. | |
| 2004/0162621 A1 | 8/2004 | Crofford | |
| 2004/0236341 A1 | 11/2004 | Petersen | |
| 2005/0010232 A1 | 1/2005 | Crofford | |
| 2005/0049714 A1 | 3/2005 | Crofford | |
| 2005/0182493 A1 | 8/2005 | Bertram, III | |
| 2005/0182496 A1 | 8/2005 | Hunter et al. | |
| 2005/0203384 A1 | 9/2005 | Sati et al. | |
| 2005/0245934 A1 | 11/2005 | Tuke et al. | |
| 2006/0149389 A1 | 7/2006 | Romagnoli | |
| 2006/0161167 A1 | 7/2006 | Myers et al. | |
| 2006/0241780 A1 | 10/2006 | McKinnon | |
| 2006/0264731 A1 | 11/2006 | Murphy | |
| 2006/0293682 A1 | 12/2006 | Justin et al. | |
| 2007/0032878 A1 | 2/2007 | Bader et al. | |
| 2007/0083214 A1 | 4/2007 | Duncan et al. | |
| 2007/0129809 A1 | 6/2007 | Meridew et al. | |
| 2007/0135927 A1 | 6/2007 | Harris et al. | |
| 2007/0161935 A1 | 7/2007 | Torrie et al. | |
| 2007/0198022 A1 | 8/2007 | Lang et al. | |
| 2007/0225818 A1 | 9/2007 | Reubelt et al. | |
| 2007/0227024 A1 | 10/2007 | Beaule | |
| 2007/0249967 A1 | 10/2007 | Buly et al. | |
| 2007/0260256 A1 | 11/2007 | Beaule | |
| 2007/0265635 A1 | 11/2007 | Torrie et al. | |
| 2007/0299452 A1 | 12/2007 | Curry | |
| 2008/0195221 A1 | 8/2008 | Howald et al. | |
| 2008/0208200 A1 | 8/2008 | Crofford | |
| 2008/0225818 A1 | 9/2008 | Niu et al. | |
| 2008/0234685 A1 | 9/2008 | Gjerde | |
| 2008/0243127 A1 | 10/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2009/0069845 A1 | 3/2009 | Frushell et al. | |
| 2009/0099570 A1 | 4/2009 | Paradis et al. | |
| 2009/0112214 A1 | 4/2009 | Philippon et al. | |
| 2009/0125108 A1 | 5/2009 | Linares | |
| 2009/0131956 A1 | 5/2009 | Dewey et al. | |
| 2009/0149965 A1 | 6/2009 | Quaid | |
| 2009/0182340 A1 | 7/2009 | Nikolchev et al. | |
| 2009/0192620 A1 | 7/2009 | Ebbitt | |
| 2009/0198274 A1 | 8/2009 | Frushell et al. | |
| 2009/0216113 A1 | 8/2009 | Meier et al. | |
| 2009/0289806 A1 | 11/2009 | Thornberry | |
| 2009/0306586 A1 | 12/2009 | Ross et al. | |
| 2009/0316967 A1 | 12/2009 | Dardenne et al. | |
| 2009/0319051 A9 | 12/2009 | Nycz et al. | |
| 2010/0016892 A1 | 1/2010 | Kaiser et al. | |
| 2010/0086186 A1 | 4/2010 | Zug et al. | |

(56) References Cited

U.S. PATENT DOCUMENTS

| | | |
|---|---|---|
| 2010/0114101 A1 | 5/2010 | Crofford |
| 2010/0152859 A1 | 6/2010 | Thompson et al. |
| 2011/0190887 A1 | 8/2011 | Shapiro |
| 2011/0238180 A1 | 9/2011 | Fritz et al. |
| 2011/0288643 A1 | 11/2011 | Linder-Ganz et al. |
| 2012/0053590 A1 | 3/2012 | Allen et al. |
| 2012/0109331 A1 | 5/2012 | Meridew et al. |
| 2012/0232656 A1 | 9/2012 | Gedet et al. |
| 2012/0232657 A1 | 9/2012 | Myung et al. |
| 2012/0283840 A1 | 11/2012 | Frederick et al. |
| 2013/0006276 A1 | 1/2013 | Lantz et al. |
| 2013/0035766 A1 | 2/2013 | Meridew |
| 2013/0211536 A1 | 8/2013 | Metzger et al. |
| 2013/0218283 A1 | 8/2013 | Samuelson et al. |
| 2013/0226311 A1 | 8/2013 | Bonutti |
| 2013/0245780 A1 | 9/2013 | Meridew et al. |

FOREIGN PATENT DOCUMENTS

| | | |
|---|---|---|
| CH | 449174 A | 12/1967 |
| EP | 0289192 A1 | 11/1988 |
| EP | 0803234 A1 | 10/1997 |
| EP | 1195149 A2 | 4/2002 |
| EP | 1263350 A1 | 12/2002 |
| EP | 1304980 A2 | 5/2003 |
| EP | 1437987 A2 | 7/2004 |
| EP | 1472997 A2 | 11/2004 |
| EP | 1472998 A2 | 11/2004 |
| EP | 1493406 A2 | 1/2005 |
| EP | 1494625 A2 | 1/2005 |
| EP | 1499268 A1 | 1/2005 |
| EP | 1506749 A2 | 2/2005 |
| EP | 1520559 A1 | 4/2005 |
| EP | 1550024 A2 | 7/2005 |
| EP | 1553898 A1 | 7/2005 |
| EP | 1628590 A1 | 3/2006 |
| EP | 1673043 A1 | 6/2006 |
| EP | 1713420 A2 | 10/2006 |
| EP | 1945146 A2 | 7/2008 |
| EP | 1954235 A2 | 8/2008 |
| EP | 1981409 A2 | 10/2008 |
| EP | 1996123 A2 | 12/2008 |
| EP | 2124764 A1 | 12/2009 |
| EP | 2152219 A1 | 2/2010 |
| EP | 2175419 A2 | 4/2010 |
| EP | 2185108 A1 | 5/2010 |
| GB | 2139098 A | 11/1984 |
| JP | 2009525767 A | 7/2009 |
| WO | 8807356 A1 | 10/1988 |
| WO | 0167999 A2 | 9/2001 |
| WO | 0209615 A2 | 2/2002 |
| WO | 0209616 A2 | 2/2002 |
| WO | 03034952 A2 | 5/2003 |
| WO | 03086242 A1 | 10/2003 |
| WO | 03086243 A2 | 10/2003 |
| WO | 03094802 A1 | 11/2003 |
| WO | 2004001569 A2 | 12/2003 |
| WO | 2004037129 A1 | 5/2004 |
| WO | 2005000140 A2 | 1/2005 |
| WO | 2005039453 A1 | 5/2005 |
| WO | 2005072231 A2 | 8/2005 |
| WO | 2006030392 A1 | 3/2006 |
| WO | 2007021806 A2 | 2/2007 |
| WO | 2007056678 A2 | 5/2007 |
| WO | 2007080454 A2 | 7/2007 |
| WO | 2007092841 A2 | 8/2007 |
| WO | 2007109291 A2 | 9/2007 |
| WO | 2008090468 A2 | 7/2008 |
| WO | 2008112996 A1 | 9/2008 |
| WO | 2008130656 A1 | 10/2008 |
| WO | 2008150731 A1 | 12/2008 |
| WO | 2009039513 A1 | 3/2009 |
| WO | 2009046547 A1 | 4/2009 |
| WO | 2009058830 A1 | 5/2009 |
| WO | 2009076293 A2 | 6/2009 |
| WO | 2009076297 A2 | 6/2009 |
| WO | 2009108683 A1 | 9/2009 |
| WO | 2009114829 A2 | 9/2009 |
| WO | 2010033473 A2 | 3/2010 |
| WO | 2010052500 A2 | 5/2010 |
| WO | 2010065901 A1 | 6/2010 |
| WO | 2010096124 A1 | 8/2010 |
| WO | 2010099247 A2 | 9/2010 |

OTHER PUBLICATIONS

Chinese Office Action; State Intellectual Property Office of People's Republic of China; Chinese Patent Application No. 201080017951.X; Jan. 14, 2015; 11 pages.

International Preliminary Report on Patentability dated Mar. 7, 2013 in Application No. PCT/US2011/049129.

International Search Report and Written Opinion dated Mar. 27, 2012 in Application No. PCT/US2011/049129.

International Search Report for PCT/US2009/056890, mailed Apr. 5, 2010.

International Preliminary Report on Patentability and Written Opinion for PCT/US2009/056890, mailed Mar. 22, 2011.

International Search Report and Written Opinion for PCT/US2010/025292, mailed Dec. 28, 2010.

International Preliminary Report on Patentability and Written Opinion for PCT/US2010/025292, mailed Aug. 30, 2011.

International Search Report for PCT/IB2006/004038, mailed Aug. 29, 2007.

Byrd, et al., "Arthroscopic Management of Femoracetabular Impingement," AAOS Instructure Course Lectures, vol. 58, 2009, pp. 231-239.

Leunig, et al., "Femoracetabular Impingement: Etiology and Surgical Concept," Operative Techniques in Orthopaedics, Jun. 5, 2005, pp. 247-255.

Leunig, et al., "Femoracetabular Impingement: Treatment of the Acetabular Side," AAOS Instructional Course Lectures, vol. 58, 2009, pp. 223-229.

European Office Action; European Patent Office; European Patent Application No. 10746801.9; Aug. 20, 2014; 8 pages.

* cited by examiner

METHODS AND APPARATUS FOR FAI SURGERIES

CROSS-REFERENCE TO RELATED APPLICATIONS

This application is a continuation of U.S. patent application Ser. No. 13/202,612, filed Apr. 16, 2012, which is a U.S. national phase filing of International Application No. PCT/US2010/025292, filed Feb. 25, 2010, which claims the benefit of U.S. Provisional Application No. 61/155,060, filed Feb. 24, 2009. The disclosures of each of these applications are incorporated by reference in their entirety.

BACKGROUND

1. Field

This invention relates generally to hip surgeries and, more particularly, relates to surgical methods, tools and implants for treating femoral acetabular impingement.

2. Related Art

Femoroacetabular impingement or FAI is a condition of the hip joint where the femoral head and acetabulum rub abnormally creating damage to the hip joint. The damage can occur to the articular cartilage of the head or acetabulum or to the labral cartilage on and around the acetabular rim.

Specifically, FAI may take one of two forms: cam or pincer. The difference between the two forms is determined by the abnormality of the hip joint that is the cause of the damage. The cam form of FAI occurs when the femoral head and neck relationship is aspherical, or not perfectly round. This loss of roundness contributes to abnormal contact between the head and socket. The pincer form occurs when the acetabulum has too much coverage of the femoral head. This over-coverage typically exists along the front-top rim of the acetabulum and results in the labral cartilage being "pinched" between the rim of the socket and the anterior femoral head-neck junction. In most cases, the cam and pincer forms exist together (thus creating a compound form of FAI).

Treatment of FAI may be accomplished by surgical intervention. Arthroscopically, the hip may be scoped to assess the hip joint and treat damage that is found through two to four 1 cm incisions. Often, all of the components of FAI such as the labral tear, damaged cartilage, and friction between the ball and socket can be treated through the arthroscope. Repair may include debridement, microfracture techniques, labral repair, and bony decompression. Care must be taken to avoid damage to the hip's blood supply during the osteoplasty procedure.

An open surgical technique requires hip dislocation through an incision (approximately 6 to 10 inches). An upper thigh bone osteotomy allows for dislocation of the femoral head from the socket exposing all parts of the joint. This exposure allows treatment of labral tears and abnormal contact between the ball and socket while protecting the blood supply to the hip. In both of these types of treatment, bone removal and repair are employed to address FAI.

SUMMARY OF THE INVENTION

It is in view of the above that the present invention was developed. In one embodiment of the invention, a partial rim implant for an acetabulum in a pelvic bone comprises a ridge, a bearing surface, and a fixation surface. The ridge is oriented to replace a labrum. The bearing surface is configured to align with the articulating surface of the acetabulum. The bearing surface extends from the ridge toward the apex of the acetabulum. The fixation surface is configured to fix the implant to a prepared bone surface of the pelvic bone.

In another aspect of the invention, the fixation surface is generally perpendicular to the articulating surface of the acetabulum.

In yet another aspect of the invention, the apex of the acetabulum has a central axis extending toward a plane defined by the rim of the acetabulum, further comprising a rim portion extending from the fixation portion to the ridge, the rim portion orienting the ridge.

Another embodiment provides an implant made of a first compliant material and a second stiffer material.

In another embodiment, the ridge of the implant is made of the first compliant material.

In yet another embodiment, the fixation surface is made of the first compliant material.

Another embodiment comprises an insertion portion extending generally perpendicularly from the bearing surface and a fixation flange extending from a rim portion of the implant. The insertion portion and the flange portion converge toward one another as the flange and insertion portion extend away from the acetabulum.

In another embodiment, the apex of the acetabulum has a central axis extending toward a plane defined by the rim of the acetabulum, the implant further comprising a transition portion located between the bearing portion and the rim portion, the transition portion extends the rim portion toward the central axis of the acetabulum.

In yet another embodiment, the implant is rolled onto the rim of the acetabulum.

Another embodiment provides a fixation surface which is a post extending into the pelvic bone.

In another embodiment, the implant is fixed to the bone with sutures.

Another aspect of the invention provides a spacer for spacing a femur from an acetabulum. The spacer comprises a spoon and a plenum. The spoon portion is configured to wrap around the head of the femur. The plenum is attached to the spoon and configured to inflate the spoon. The spoon, when inflated, separates the acetabulum from the femur.

In another embodiment, the spoon further comprises a cutout portion configured to extend around the ligamentum teres.

In yet another embodiment, the spacer further comprises a stiff portion extending through the spoon, such that the spoon may be pushed into the hip joint.

Another embodiment provides for the stiff portion to extend around the periphery of the spoon.

Another aspect of the invention provides a cutting guide for cutting a portion of a rim of an acetabulum. The guide comprises a generally planar rectangular member and an axis. The generally rectangular planar member has an opening in the central portion. Edges of the opening form a cutting surface. The opening has a width and a height. The axis extends across the planar member. The axis forms a fold line upon which the planar member may be folded such that when the planar member is folded over an acetabular rim, the edges of the opening extend over the rim and are configured to direct a cutting member to remove bone to a depth defined by the height of the opening.

In another embodiment, the width of the opening is set to the width of the implant.

In yet another embodiment, the fold line is curved.

Another embodiment provides the curved fold line is curved relative to the radius of the acetabulum.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings.

DETAILED DESCRIPTION OF THE EMBODIMENTS

Figure 1:
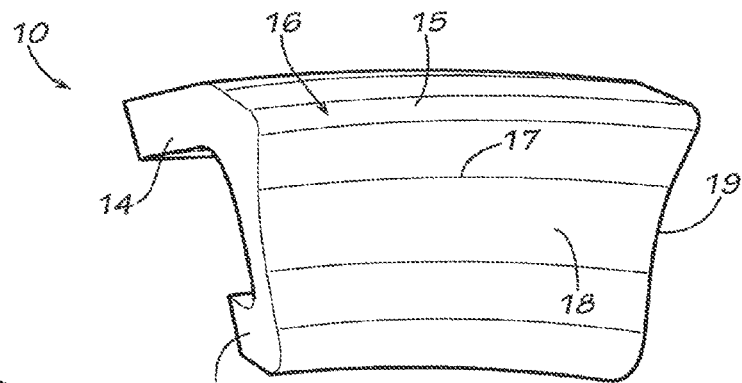
FIG. 1 is a view of an embodiment of an acetabular implant for treating FAI.
Figure 2:
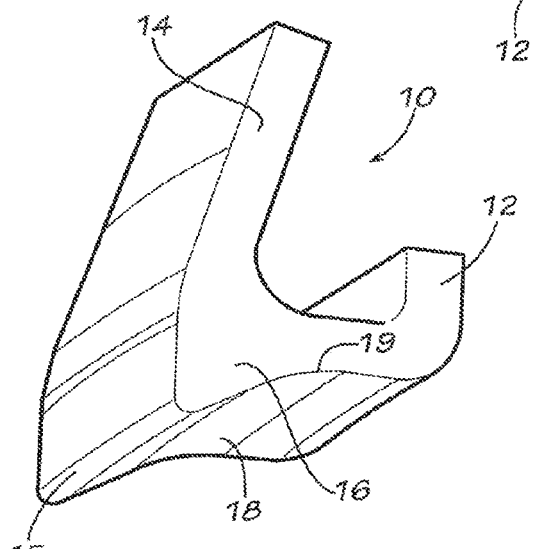
FIG. 2 is another view of the embodiment of FIG. 1.
Figure 3:
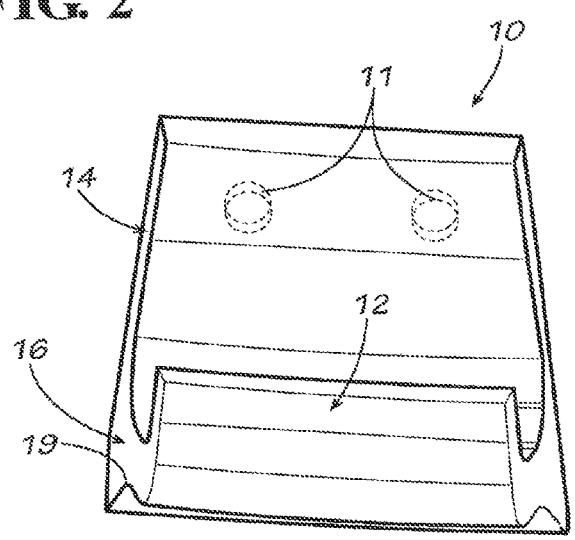
FIG. 3 is another view of the embodiment of FIG. 1.

Referring to the accompanying drawings in which like reference numbers indicate like elements, FIG. 1 is a view of an embodiment of an acetabular implant 10 for treating FAI. The implant 10 has an insertion portion 12, a flange portion 14, a ridge 15, a rim portion 16, a rim curvature 17, a bearing surface 18 and a rim-bearing transition 19. For additional views of this embodiment, FIG. 2 is another view of the embodiment of FIG. 1 and FIG. 3 is yet another view of the embodiment of FIG. 1. In FIG. 3, mounting holes 11 are positioned on the flange portion 14. The insertion portion 12 may be configured to insert into the acetabulum generally perpendicular to the bearing surface of the acetabulum. The bearing surface 19, then, would lie generally flush with the bearing surface of the acetabulum. The rim-bearing transition 19 may generally be a curved portion of the bearing surface 19 that transitions the bearing surface 19 into the rim portion 16. The rim portion 16 extends inward toward a central axis of the acetabulum from the bearing surface 19. This rim portion 16 may then be used to help capture the head of the femur (which was the function of the surface that was removed, albeit the removed surface was damaged necessitating its removal. Thus, the implant may restore the function of the damaged surfaces that were removed without causing the negative pathological response that was generated from the damaged tissue, bone or cartilage.

The rim portion 16 has a ridge that transitions the rim portion 16 from the bearing surface side of the implant 10 to a fixation side (through the flange portion 14). The flange portion 14 may be fixed to the acetabulum by screws or pins through screw holes 11 (as shown in this embodiment) or by other means as discussed with respect to other embodiments. The rim curvature 17 of the implant 10 is sized to fit the acetabulum. Thus, varying diameters of different acetabulums may require various rim curvatures 17 of the implant. Additionally, depending on the size of the damaged region, the thickness of the implant 10, the width of the implant 10 and the depth of the rim portion 16 may be changed to fit the specific anatomy of the patient.

The embodiments generally share some common features, namely, a bearing portion, a rim portion for replacing the labrum, and a fixation portion. It is contemplated within the scope of this disclosure that different variations as described herein may achieve a desired implant embodiment by providing these features as described and then combined.

Figure 4A:
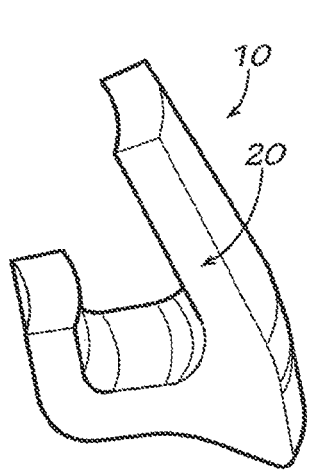
FIGS. 4A through 4F are views of embodiments of an acetabular implant similar to the embodiment of FIG. 1.
Figure 4B:
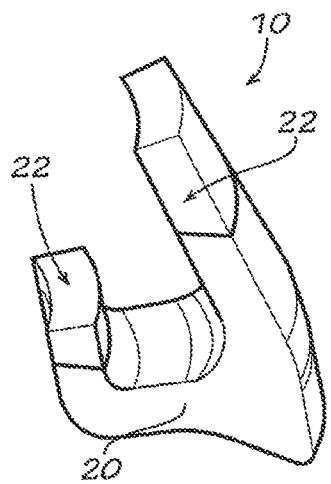
Figure 4C:
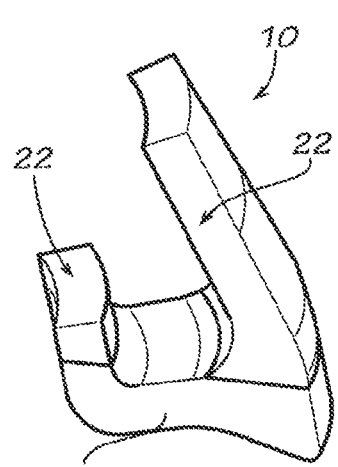
Figure 4D:
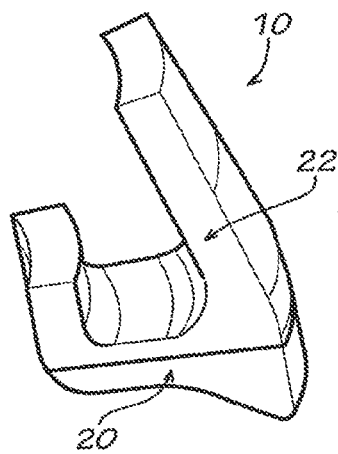
Figure 4E:
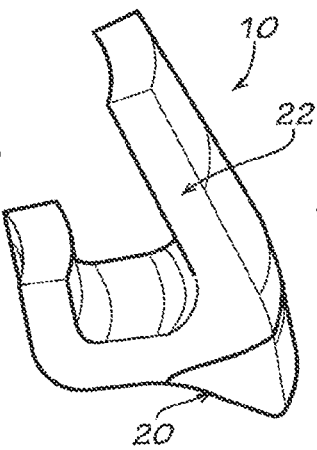
Figure 4F:
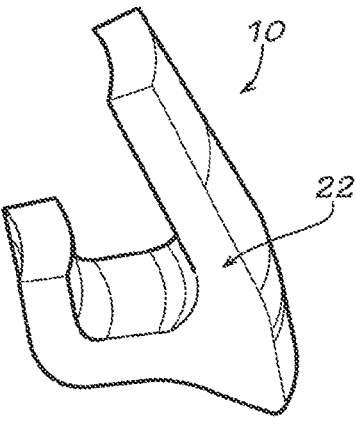

FIGS. 4A through 4F are views of embodiments of acetabular implant 10 similar to the embodiment of FIG. 1. These embodiments allow for different materials to be used for different regions of the implant 10. A first stiffer material portion 20 (e.g. metal, porous material, or PEEK) may be used for portions of the bearing surface while a more flexible, compliant material portion 22 (e.g., polyurethane) may be used for the flanges and bone interfacing surfaces. Such embodiments may give the structure necessary to perform the functions of the implant 10 while allowing for a more conforming contact surface between the implant and the acetabulum. The amount of one type of material vrealtive to the other may be determined by the dynamics of the particular joint. For example, in FIG. 4B, the majority of the implant is made from the stiffer material 20. In such an embodiment, the dynamics may produce larger loads across the implant than an implant such as the one shown in FIG. 4E, where only the rim portion is made of the stiffer material 20. A continuum between exerted loads, implant stiffness, and conformity may all contribute to the material composition of the implant 10 such that an implant may be made from a stiffer material 20 (shown in FIG. 4A) or entirely from the more compliant material (as shown in FIG. 4F).

Figure 5B:
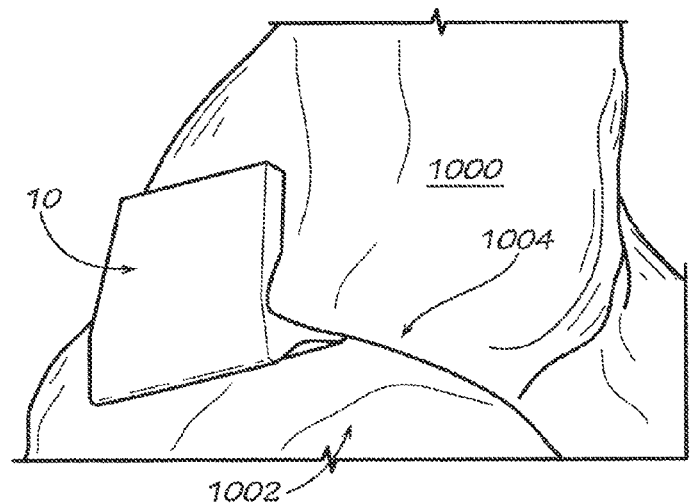
FIGS. 5A and 5B are views of the implant of FIG. 1 on an acetabulum.
Figure 5A:
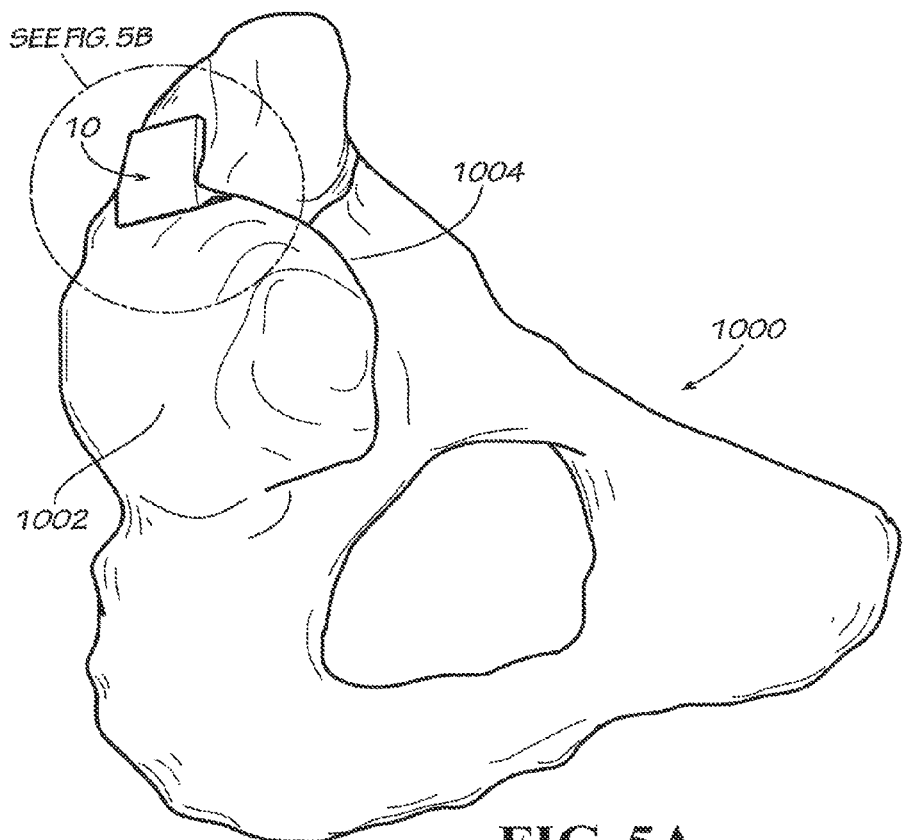

FIGS. 5A and 5B are views of the implant 10 of FIG. 1 on an acetabular rim 1004 in the acetabulum 1002 of a pelvic bone 1000. As previously described, the implant 10 extends over the rim of the acetabulum 1004. The rim portion 16 of the implant 10 is positioned to generally extend toward a central axis of the acetabulum (or at least to not continue to extend the spherical features of the acetabulum more.) As shown in this embodiment, there are no screw holes extending through the flange portion of the implant 10. Fixation means, if necessary, may be accomplished through a bone ingrowth surface on the implant 10, or by other mechanical means.

Figure 6:
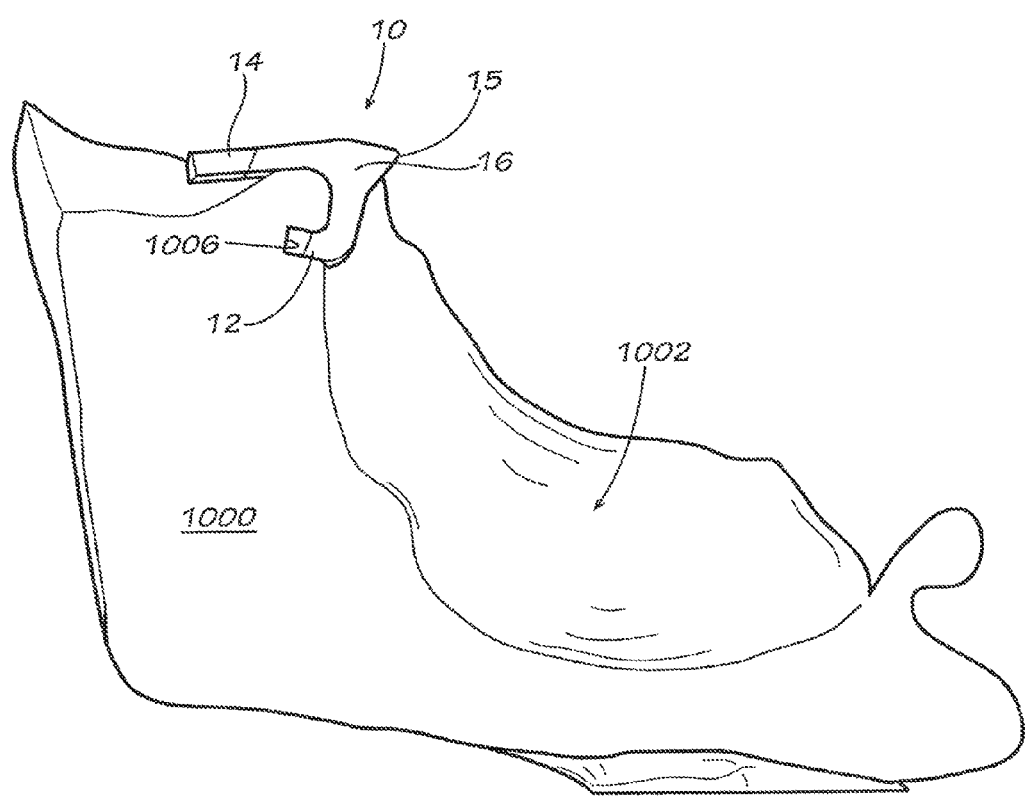
FIG. 6 is a cut away view of the implant and acetabulum of FIG. 5.

FIG. 6 is a cut away view of the implant and acetabulum of FIG. 5. The implant 10 is fixed to the acetabulum by a mechanical interference fit. The portions 12 and 14 converge toward one another in the pelvic bone. Thus, once the implant is put on the bone, the implant will not dislodge as the converging surfaces grip the bone in between the insertion portion 12 and the flange 14. Such an interference fit may be achieved by rolling the implant 10 from inside the acetabulum 1002 over the rim. Such a method requires the insertion portion 12 to first engage the bone, then rolling the flange 14 over the top of the bone.

Figure 7A:
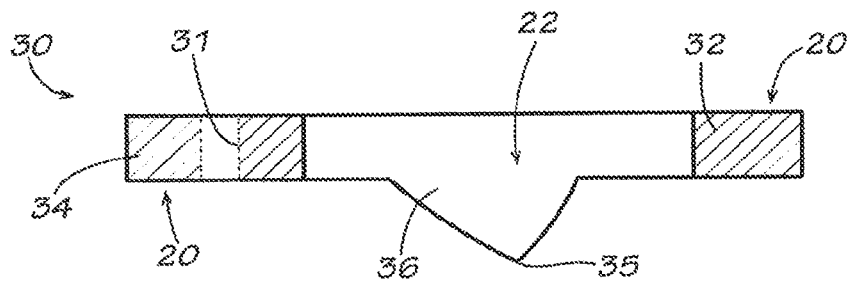
FIG. 7A is a view of another embodiment of an acetabular implant for treating FAI.
Figure 7B:
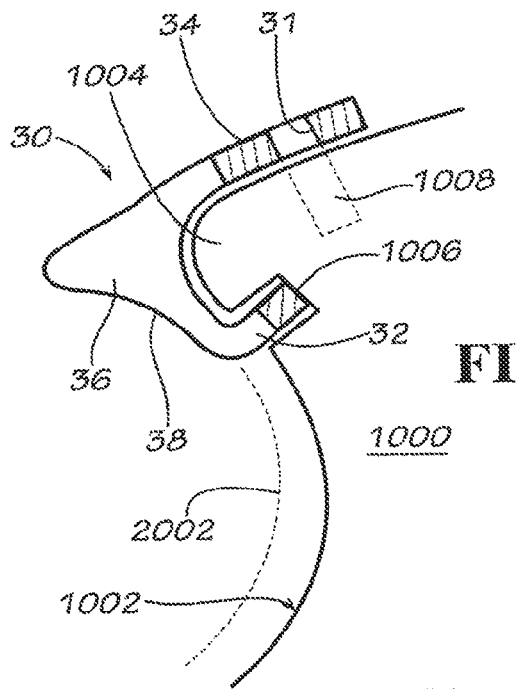
FIGS. 7B and 7C are views of the embodiment of FIG. 7A attached to an acetabulum.
Figure 7C:
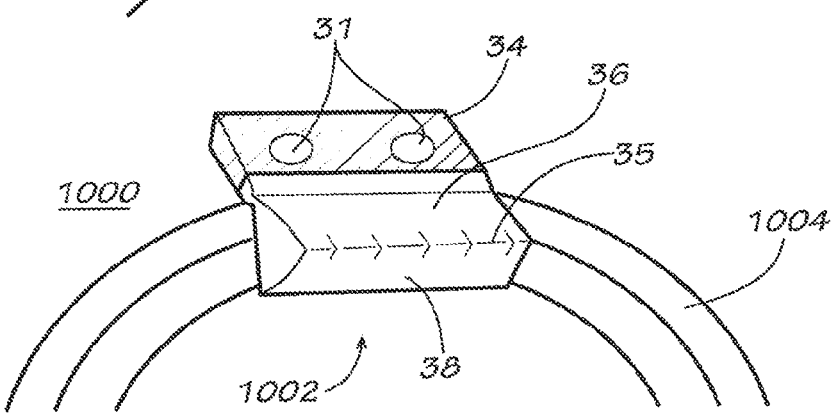

FIG. 7A is a view of another embodiment of an acetabular implant for treating FAI. This bi-material implant 30 also has stiffer portions 20 and more flexible portions 22. The more flexible portions, however, comprise the fixation portions of the implant 30, which in this example is the insertion portion 32 and the flange portion 34. The implant 30, then may be wrapped around the rim of the acetabulum. As shown in FIGS. 7A and 7B, FIG. 7B and 7C are views of the embodiment of FIG. 7A attached to an acetabulum 1000. The insertion portion 32 may be put into a prepared recess portion 1006 of the acetabulum. The flexible portion 22 may then be wrapped around the rim and fixed to the acetabulum (for example through a mounting hole 31) to the acetabulum 1000. A more flexible bearing portion 38 and rim portion 36 may then be positioned to adjust to the proper depth to keep the bearing surface 38 of the implant 30 in line with the natural bearing surface of the acetabulum and may also position a ridge 35 of the rim portion 36 to be properly oriented to provide the capture features that are replaced with the implant 30.

Figure 8B:
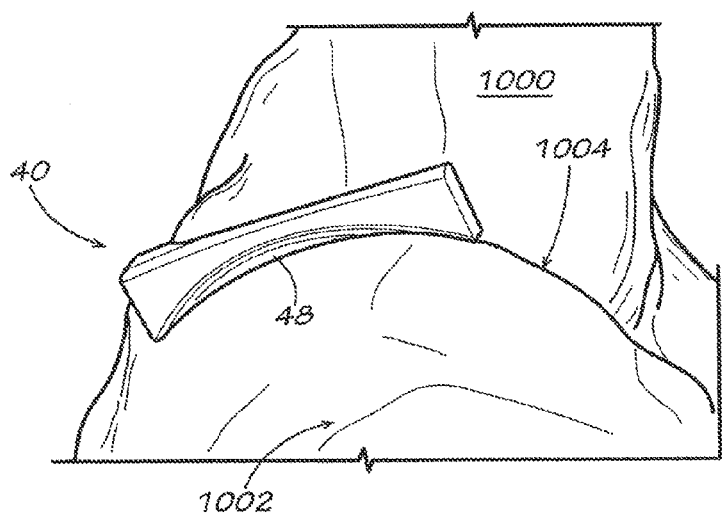
FIGS. 8A and 8B are views of another embodiment of an acetabular implant for treating FAI implanted on an acetabulum.
Figure 8A:
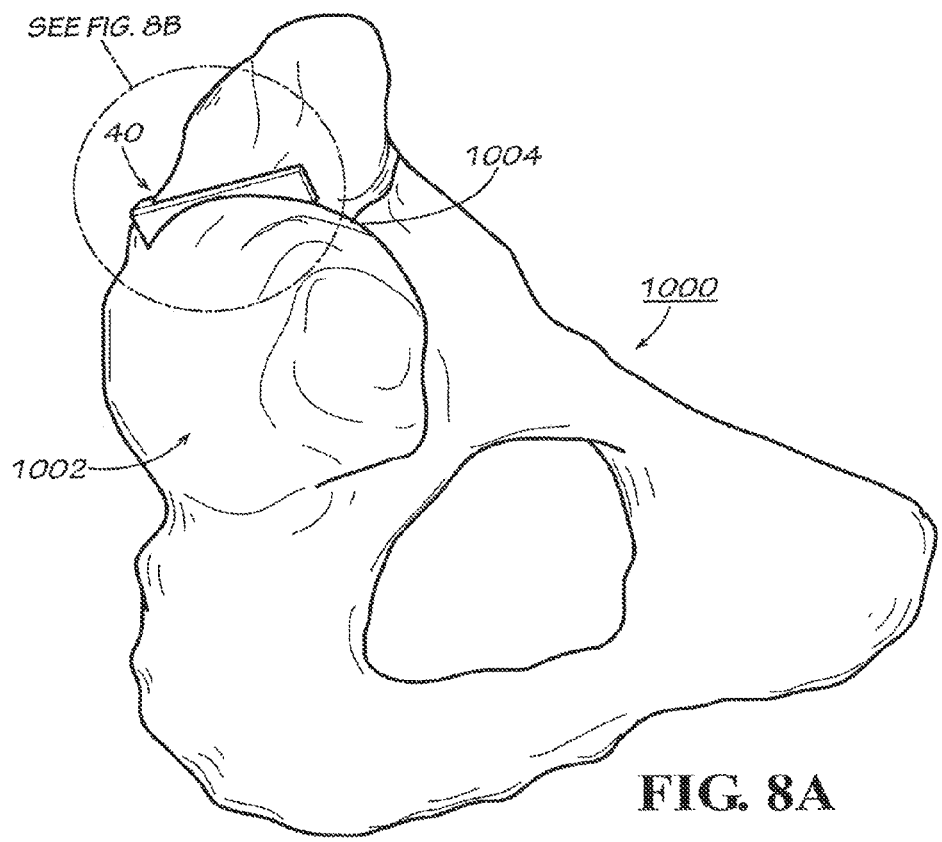

FIGS. 8A and 8B are views of another embodiment of an acetabular implant 40 for treating FAI implanted on an acetabulum 1002. This embodiment may be a hard bearing material (such as Oxinium) that may be press fit into the bone. Such an embodiment may require very precise bone preparation and a specifically sized match for the shape of the preparation accounting for the natural characteristics of the acetabulum 1002. The bearing surface 48 of the implant 40 may then be a hard bearing just as the whole implant 40 is a hard material. The bone for receiving such an implant may be prepared with an instrument having the shape desired for the bone contacting surface of the implant 40 so that the preparation may occur at one time, instead of a more fitted procedure where different portions of bone may be prepared based upon earlier preparation of other bone portions. The implant 40 may be under constant compressive load so that there is little risk of dislodging of the implant 40 from the acetabulum.

Figure 9A:
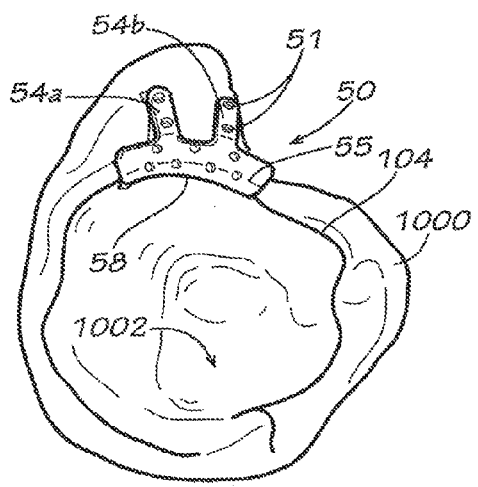
FIG. 9A is a view of another embodiment of an acetabular implant for treating FAI implanted on an acetabulum.
Figure 9B:
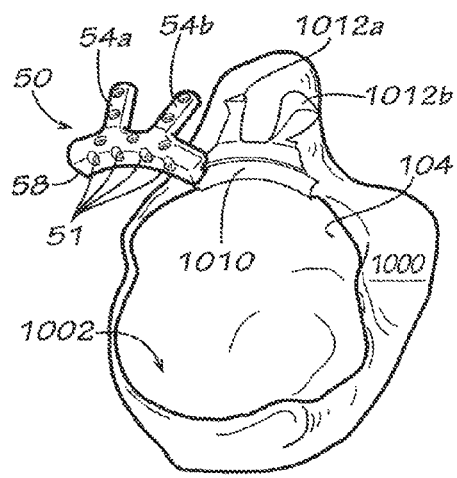
FIG. 9B is an exploded view of the acetabulum and implant of FIG. 9A.

FIG. 9A is a view of another embodiment of an acetabular implant 50 for treating FAI implanted on an acetabulum. FIG. 9B is an exploded view of the acetabulum and implant 50 of FIG. 9A. Mounting holes 51 may be positioned on flanges 54a and 54b to mount the implant 50 to the bone. A ridge 55 on a rim portion of the implant 50 provides the constraining feature of the implant 50. A bearing surface 58 extends into the acetabulum to mate with the natural bearing surface of the acetabulum. In the cutaway view of FIG. 9B, bone preparation surfaces 1010, 1012a and 1012b are prepared to receive the implant 50.

Figure 10A:
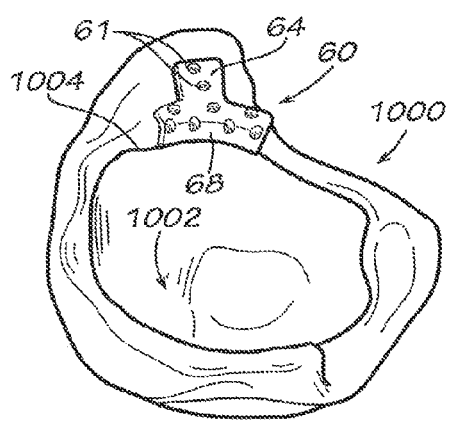
FIG. 10A is a view of another embodiment of an acetabular implant for treating FAI implanted on an acetabulum.
Figure 10B:
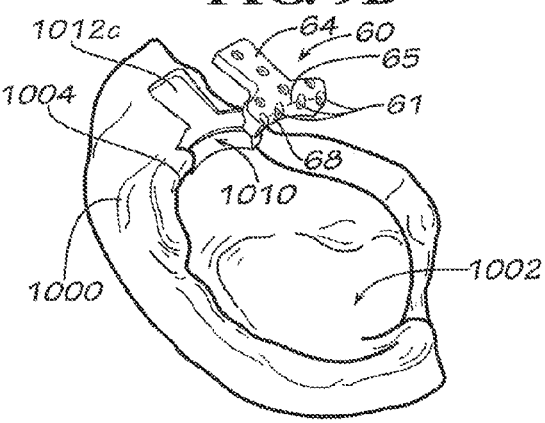
FIG. 10B is an exploded view of the acetabulum and implant of FIG. 10A.

FIG. 10A is a view of another embodiment of an acetabular implant 60 for treating FAI implanted on an acetabulum. FIG. 10B is an exploded view of the acetabulum and implant 60 of FIG. 10A. Mounting holes 61 may be positioned on flange 64 to mount the implant 60 to the bone. A ridge 65 on a rim portion of the implant 60 provides the constraining feature of the implant 60. A bearing surface 68 extends into the acetabulum to mate with the natural bearing surface of the acetabulum. In the cutaway view of FIG. 9B, bone preparation surfaces 1010, 1012c are prepared to receive the implant 60.

Figure 11:
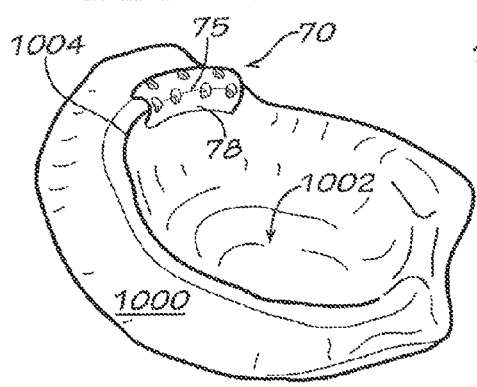
FIG. 11 is a view of another embodiment of an acetabular implant for treating FAI implanted on an acetabulum.
Figure 12:
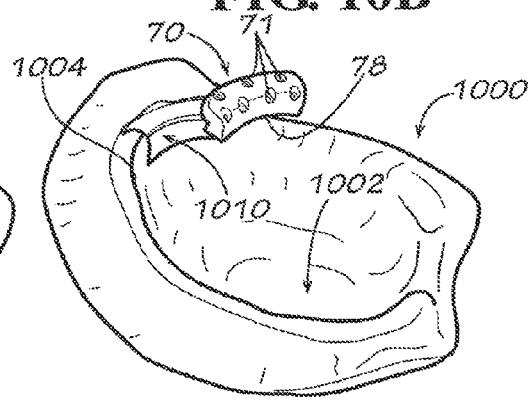
FIG. 12 is an exploded view of the acetabulum and implant of FIG. 11.

FIG. 11 is a view of another embodiment of an acetabular implant 70 for treating FAI implanted on an acetabulum. FIG. 12 is an exploded view of the acetabulum and implant 70 of FIG. 11. Mounting holes 71 may be positioned on the implant 70 to mount the implant 70 to the bone. A ridge 75 on a rim portion of the implant 70 provides the labrum replacement feature of the implant 70. A bearing surface 78 extends into the acetabulum to mate with the natural bearing surface of the acetabulum. In the cutaway view of FIG. 9B, bone preparation surfaces 1010 are prepared to receive the implant 70.

In the embodiments of FIG. 9A through FIG. 12, the bone preparation matches the implant surfaces without a compliant material in use. Thus the bone preparation would likely be from guided stamps or cutting surfaces, and not from free hand cutting using burrs or the like. As the prepared surfaces direct the position of the entire implant, the prepared surfaces must take into account not only the underlying bone but also the rim characteristics and bearing surface characteristics of the implant.

Figure 13:
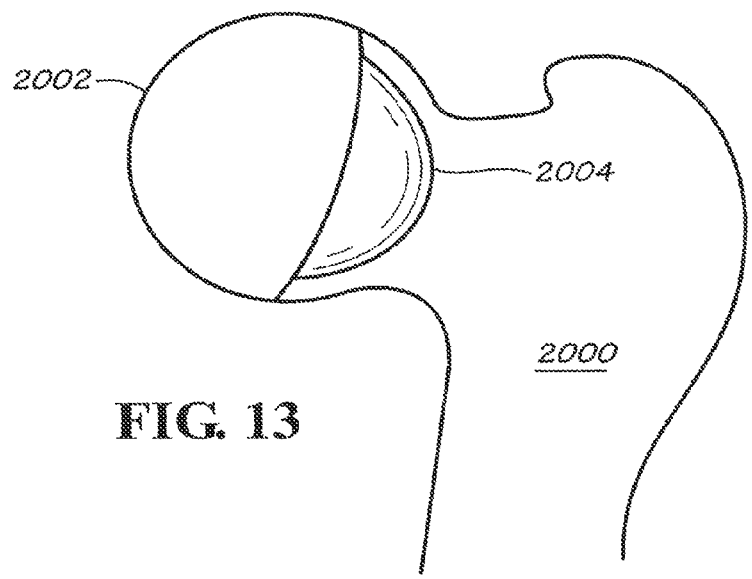
FIG. 13 is a view of a femur showing the affected area for cam type FAI.
Figure 14A:
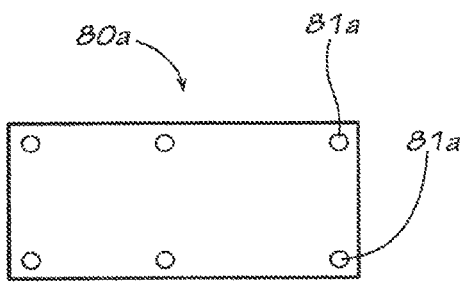
FIGS. 14A through 14D are views of embodiments of femoral implants for treating FAI on the femur.
Figure 14B:
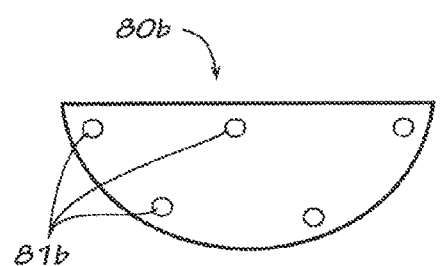
Figure 14C:
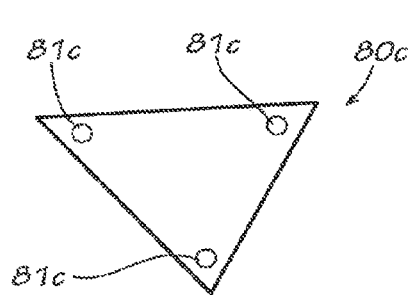
Figure 14D:
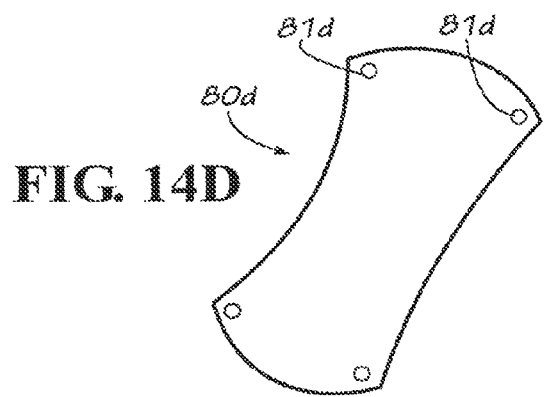

FIG. 13 is a view of a femur 2000 showing an affected area 2004 for cam type FAI. An a spherical femoral head 2002 may create the affected area 2004. It may be necessary to treat the affected area first with debridement and then with an implant designed to limit osseus overgrowth (as would occur from continued stress from contact with the acetabulum. FIGS. 14A through 14D are views of embodiments of femoral implants 80a, 80b, 80c, and 80d for treating FAI on the femur. Mounting holes 81a, 81b, 81c, and 81d may be used to mount the implant onto the femur. Alternatively, the implant shape may be molded intraoperatively or from radiographic scans of the femur prior to surgery. The implants may be made of a rigid or flexible material and mounted with any of the mounting means discussed herein.

Figure 15:
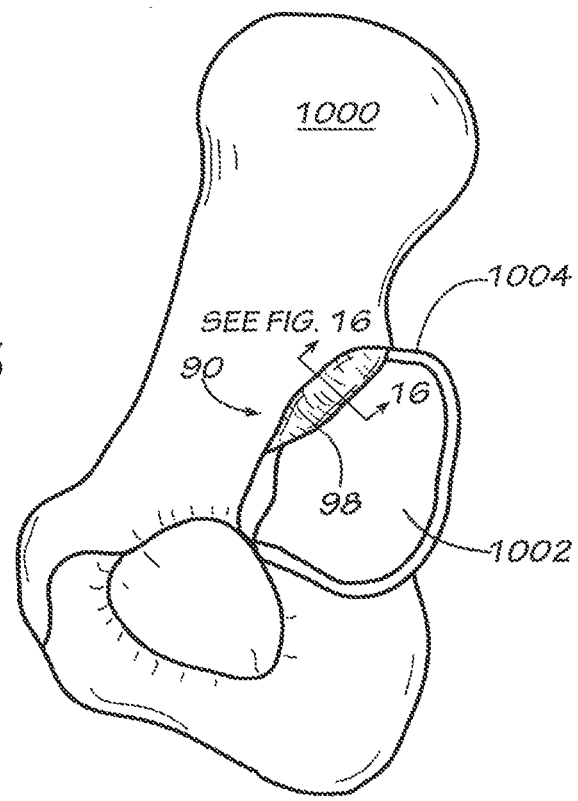
FIG. 15 is a view of another embodiment of an acetabular implant for treating FAI implanted on an acetabulum.
Figure 16:
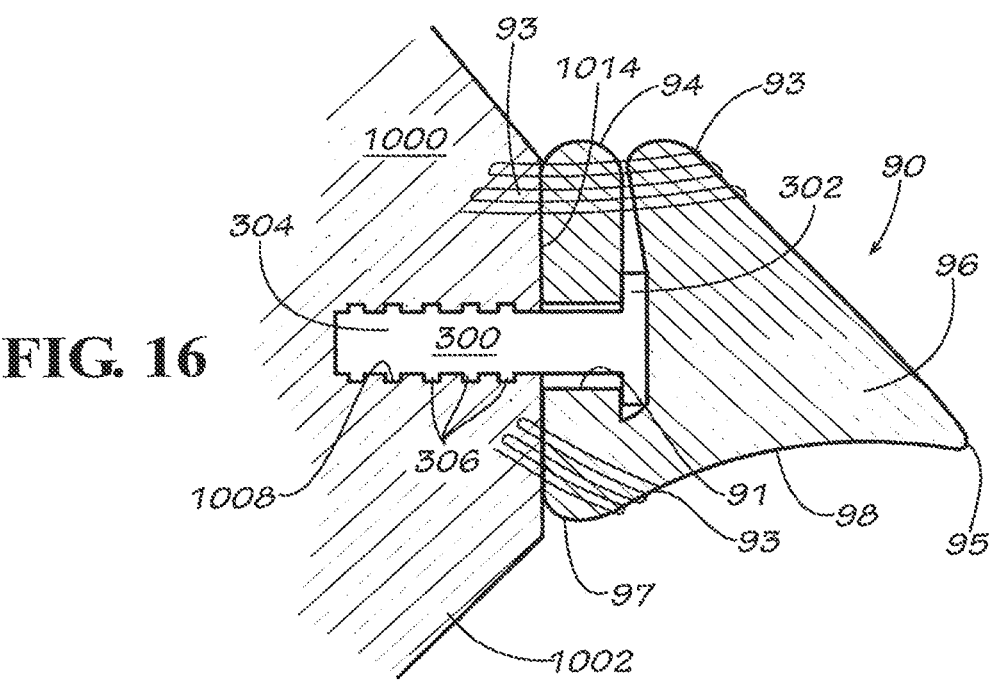
FIG. 16 is a cutaway view of the embodiment of FIG. 15.

FIG. 15 is a view of another embodiment of an acetabular implant 90 for treating FAI implanted on an acetabulum. FIG. 16 is a cutaway view of the embodiment of FIG. 15. The implant 90 is made from a flexible material that may bend at a transition 97 so that a screw 300 having a head 302 greater in diameter than a hole 91 through a flange portion 94 of the implant 90 may fix the implant to the bone. A ridge 95 of a rim portion 96 replaces the labrum. A bearing surface 98 contacts the femoral head. The transition 97 also transitions the bearing surface between the acetabulum 1002 and the bearing surface 98 of the implant 90.

The bone preparation may include a single planar surface cutting a portion of the rim of the acetabulum away. The screw 300, then, may compress the flange 94 against a bone surface 1014 to fix the implant 90 to the bone through fixation elements 306 on a shaft 304 of the screw 300. The rim portion 96 of the implant 90 may then be moved into position over the screw head 302. The rim portion 96 may also be fixed to the flange 94 with sutures or other fixation elements so that the rim portion 96 is stiffened relative to the flange 94.

Figure 17:
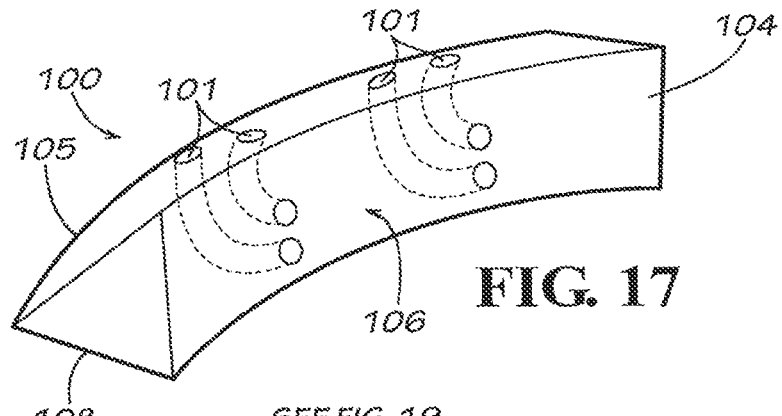
FIG. 17 is a view of another embodiment of an acetabular implant for treating FAI.
Figure 18:
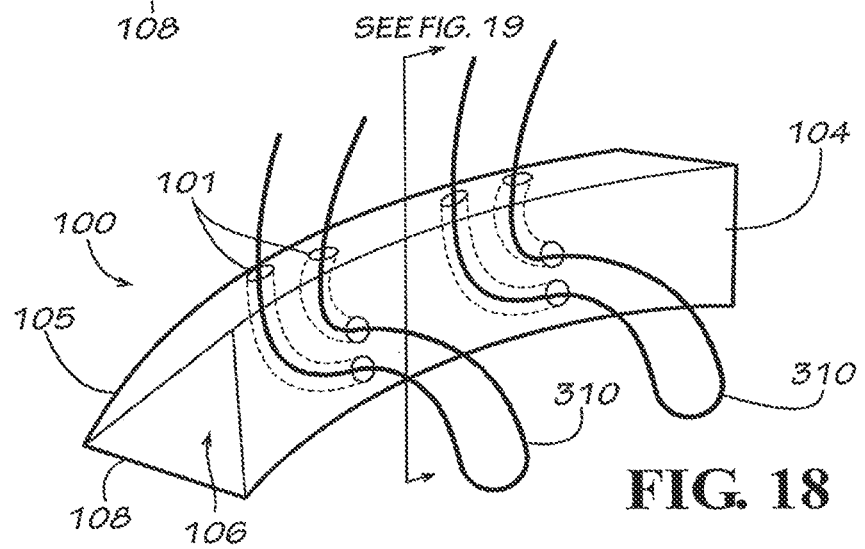
FIG. 18 is a view of the embodiment of FIG. 17 with sutures.
Figure 19:
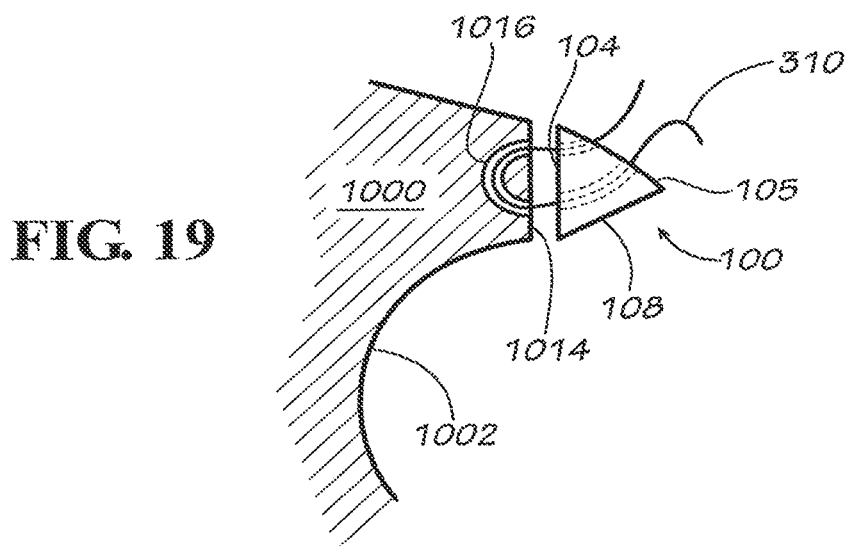
FIG. 19 is a view of the embodiment of FIG. 17 with sutures attached to an acetabulum.

FIG. 17 is a view of another embodiment of an acetabular implant 100 for treating FAI. This wedge type implant (similar to the implant of FIG. 15) may be implanted after having made a single planar cut of the acetabular rim. The implant 100 of FIG. 17, as well as FIGS. 18 and 19, may be fixed to the acetabulum with sutures or wire. FIG. 18 is a view of the embodiment of FIG. 17 with sutures 310. FIG. 19 is a view of the embodiment of FIG. 17 with sutures 310 attached to an acetabulum 1002. The sutures 310 may extend through suture guides 101 through the implant 100 and into suture guides 1016 in the bone. A bone mating surface 104, a rim portion 106, terminating in a ridge 105 extends along a bearing surface 108. Thus there is labrum replacement in a rim portion, a bearing surface transitioning to the natural cartilage in the acetabulum, and fixation means in the implant 100.

Figure 20:
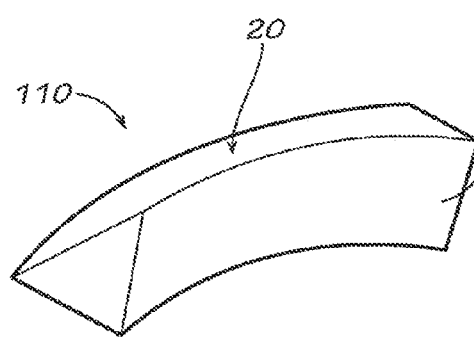
FIG. 20 is a view of another embodiment of an acetabular implant for treating FAI.
Figure 21:
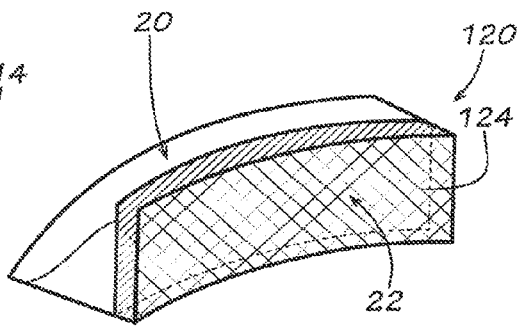
FIG. 21 is a view of another embodiment of an acetabular implant for treating FAI.
Figure 22:
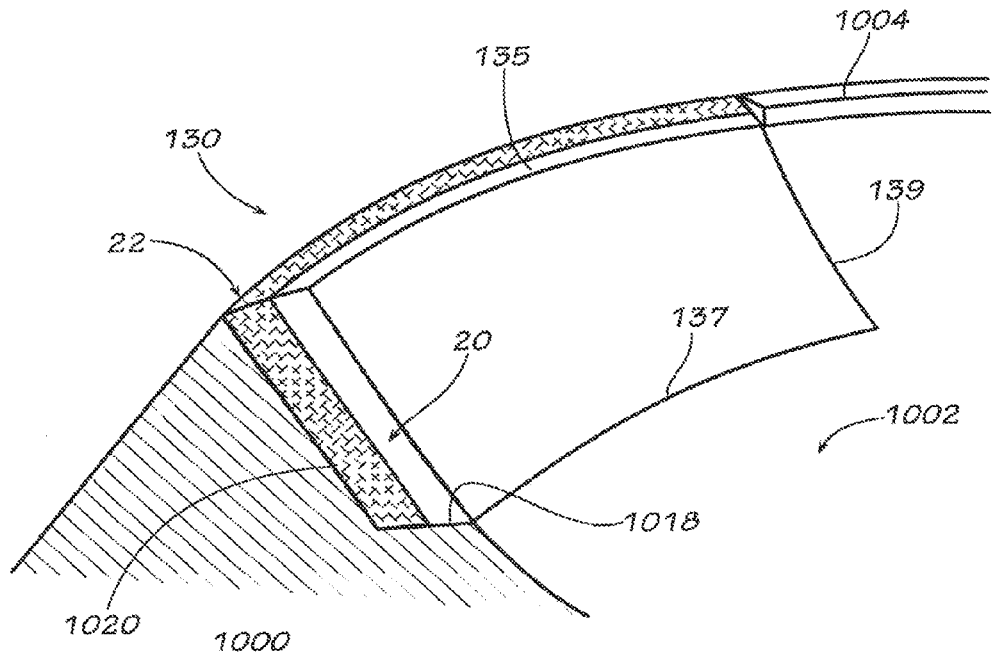
FIG. 22 is a view of another embodiment of an acetabular implant for treating FAI implanted on an acetabulum.
Figure 23:
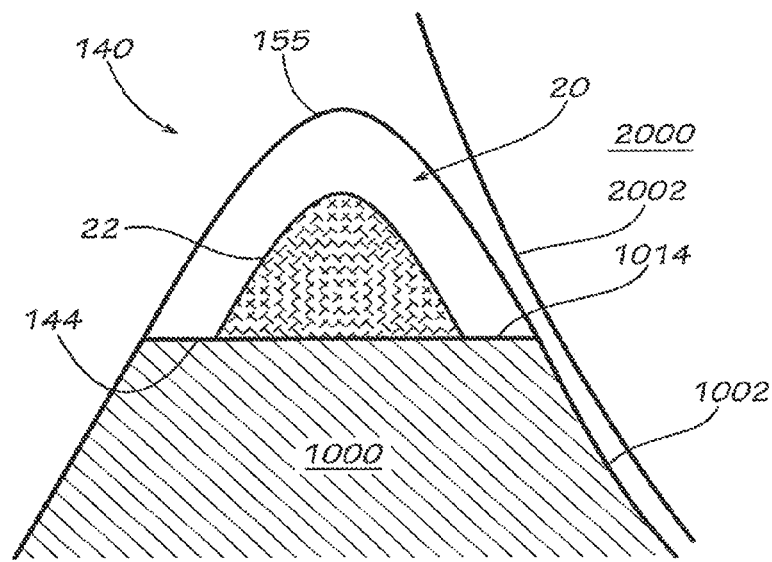
FIG. 23 is a view of another embodiment of an acetabular implant for treating FAI implanted on an acetabulum.
Figure 24:
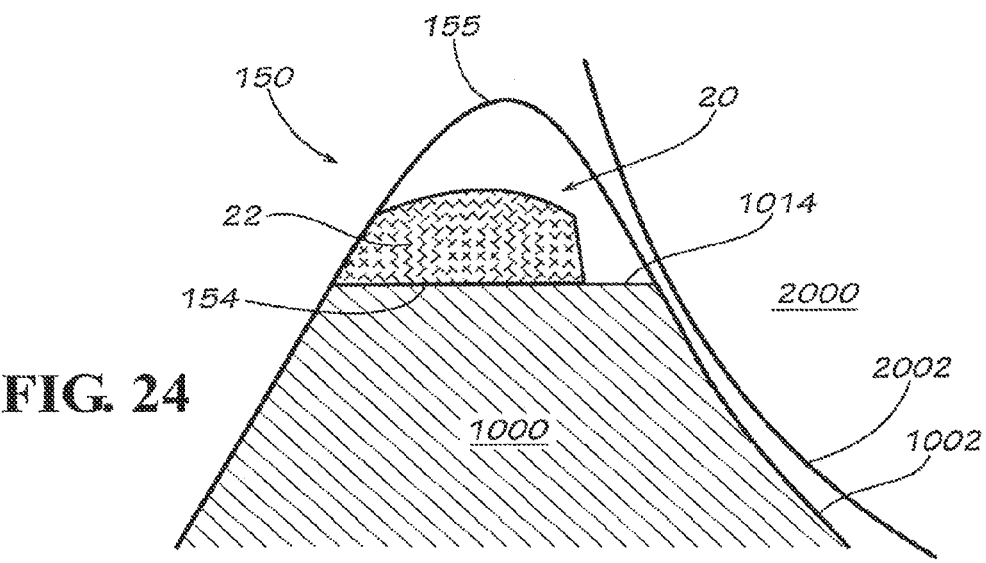
FIG. 24 is a view of another embodiment of an acetabular implant for treating FAI implanted on an acetabulum.

FIGS. 20 and 21 are views of other embodiments of an acetabular implant for treating FAI. Similar to previous embodiments, this embodiment is a wedge type design with a bi-material structure. A more rigid portion 20 and a more flexible portion 22. As previously described, such features may give the implant some compliance when implanted. As shown in FIG. 22, FIG. 22 is a view of another embodiment of an acetabular implant for treating FAI implanted on an acetabulum where the compliant material 22 is a bone interface surface. FIGS. 23 and 24 similarly show bi-material combinations where the more compliant and more rigid portions of the implant comprise different portions of the implants.

Figure 25:
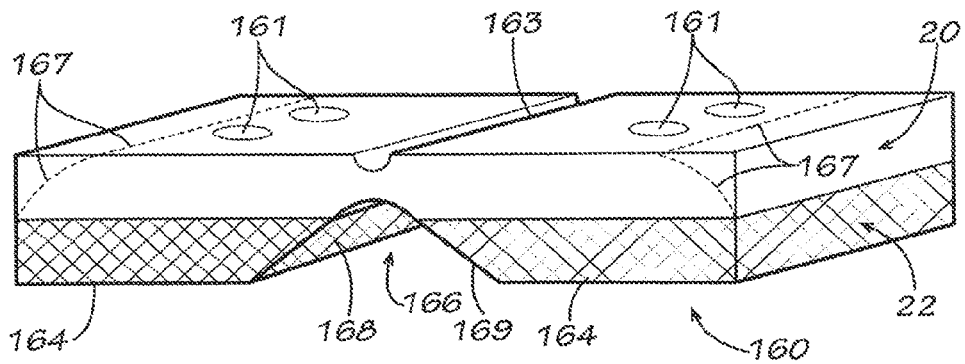
FIG. 25 is a view of another embodiment of an acetabular implant for treating FAI.

FIG. 25 is a view of another embodiment of an acetabular implant 160 for treating FAI. The implant includes more rigid material 20 and more flexible material 22. Mounting means 161 may fix the implant to the bone. A notch 166 may allow the implant to be bent. A relief 163 may be positioned opposite the notch 166 to relieve stress in the implant when it is bent. Opposing surfaces 168 and 169 may contact each other when the implant is bent. In an alternative embodiment, a chamfer 167 may transition the bearing surface of the implant to the bone.

Figure 26:
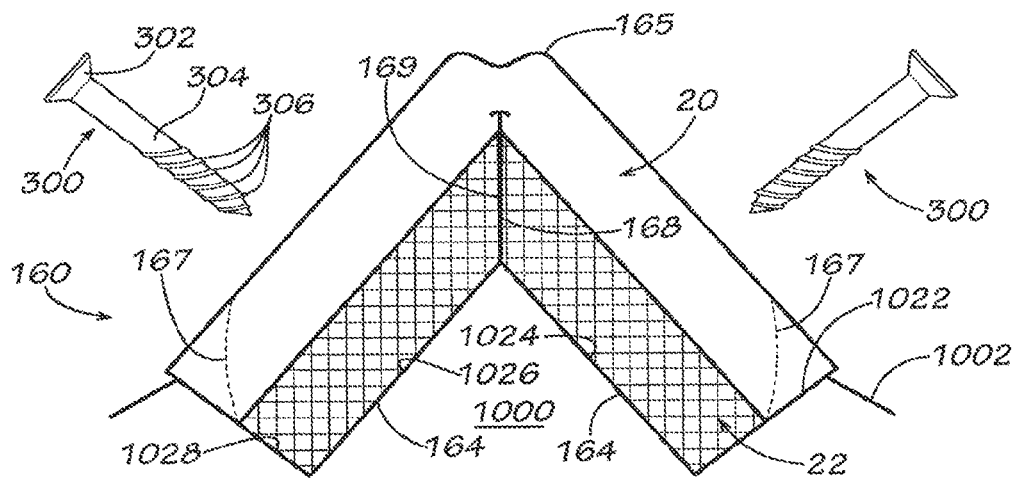
FIG. 26 is an exploded view of the implant of FIG. 25 bent into the proper shape for implantation and fixation screws.
Figure 27:
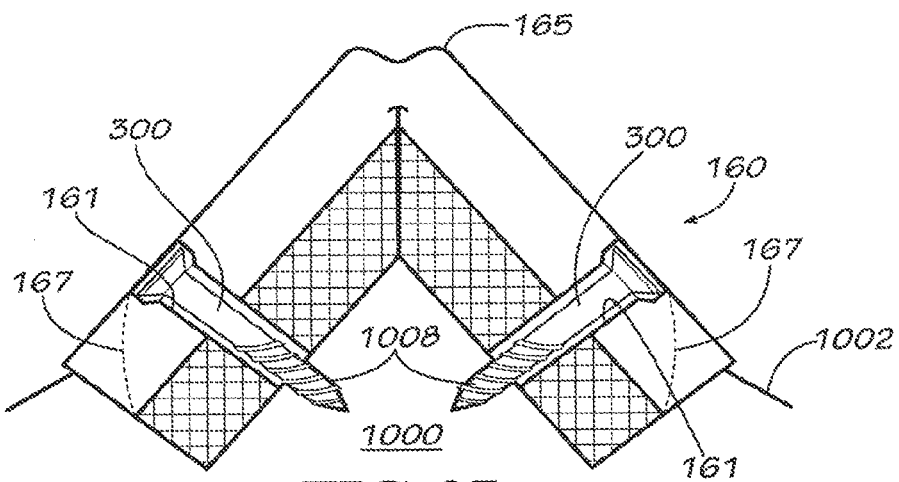
FIG. 27 is a cutaway view of the implant and screws of FIG. 26.

FIG. 26 is an exploded view of the implant of FIG. 25 bent into the proper shape for implantation and fixation screws. FIG. 27 is a cutaway view of the implant and screws of FIG. 26. The implant may form bone interfacing surfaces 1024 and 1026 to contact the bone. Screws 300 may then pass through the mounting means 161 to fix the implant 160 to the acetabulum 1002. A ridge 165 is formed when the implant is bent onto the acetabulum 1002.

Figure 28:
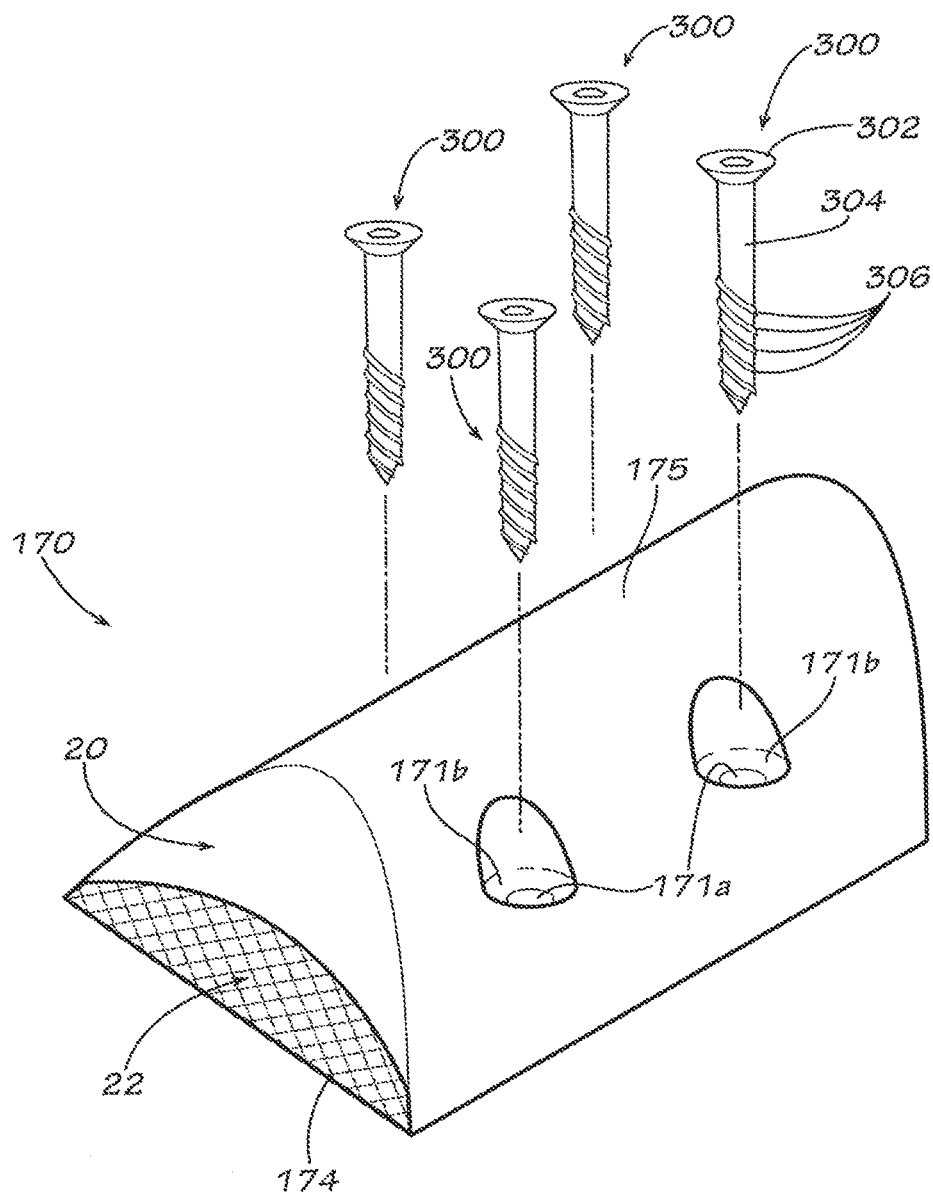
FIG. 28 is an exploded view of an embodiment of an acetabular implant and fixation screws.

FIG. 28 is an exploded view of an embodiment of an acetabular implant 170 and fixation screws 300. The implant may be made of a bi-material of more rigid material 20 and more flexible material 22. The screws 300 may be countersunk 171b with mounting holes 171a. A ridge 175 may replace the labrum when the implant is fixed to bone.

Figure 29:
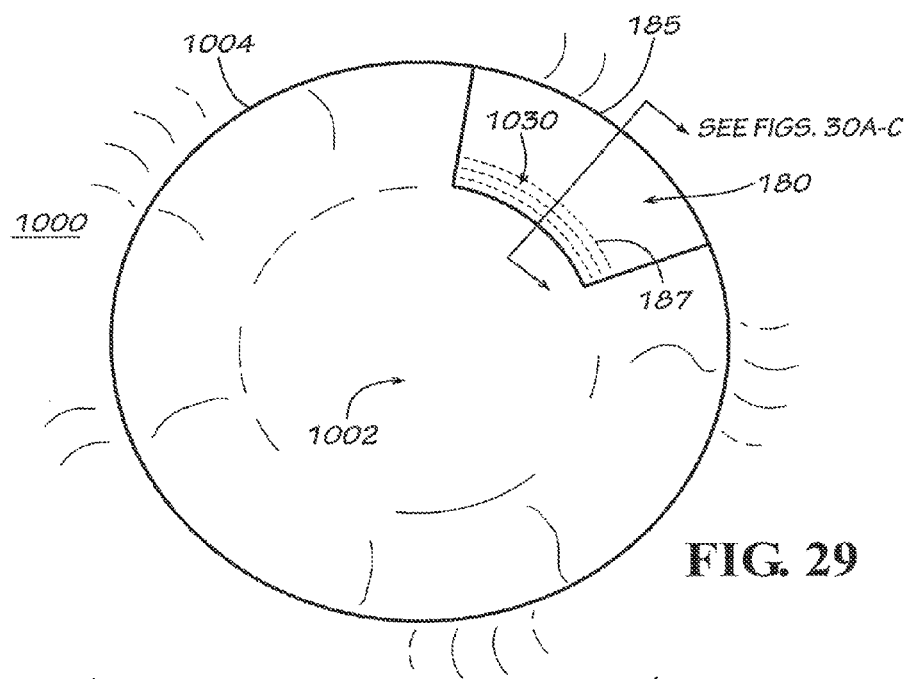
FIG. 29 is a view of an acetabulum with an implant.

FIG. 29 is a view of an acetabulum 1002 with an implant 180. The implant 180 may include a chamfer 187 between the bearing surface of the implant 180 and the articulating surface of the acetabulum. The implant may have a bone interfacing surface that runs more generally parallel to the articulating surface of the acetabulum. Two cuts that are generally perpendicular to each other form a generally rectangular recess in the bone. The load on the bone surface may be preferable in some instances with an implant design like this (as opposed to a wedge embodiment or a layover embodiment.) The general portions are still intact in such a design, namely, a bone contacting surface, a bearing surface and a constraining portion that replaces the labrum.

Figure 30A:
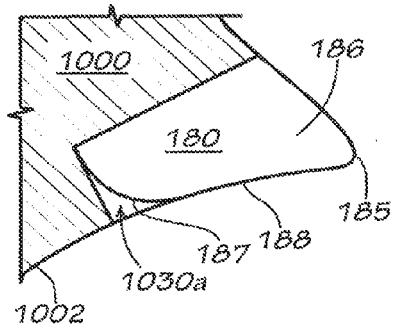
FIG. 30A is a view of an embodiment of an implant that may be implanted as shown in FIG. 29.
Figure 30B:
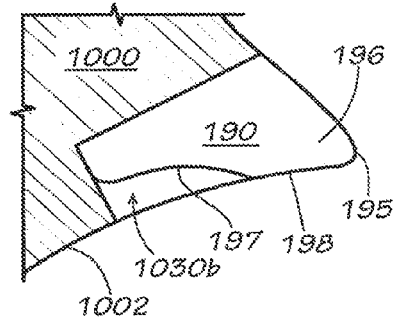
FIG. 30B is another view of an embodiment of an implant that may be implanted as shown in FIG. 29.
Figure 30C:
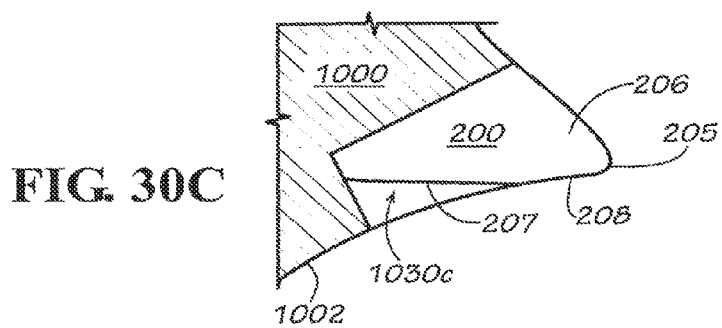
FIG. 30C is another view of an embodiment of an implant that may be implanted as shown in FIG. 29.

FIGS. 30A through 30C are views of embodiments of implants 180, 190, and 200 that may be implanted as shown in FIG. 29. In the implants a chamfer 187, 197 and 207 relieves the implant near the acetabular articulating surface and a gap 1030a, 1030b, and 1030c is formed between the implant and the acetabulum. A bearing surface 188, 198 and 208 aligns with the acetabular articulating surface. A rim portion 186, 196, and 206 extends into the acetabular cavity and terminates in a ridge 185, 195 and 205 that replaces the labrum.

Figure 31:
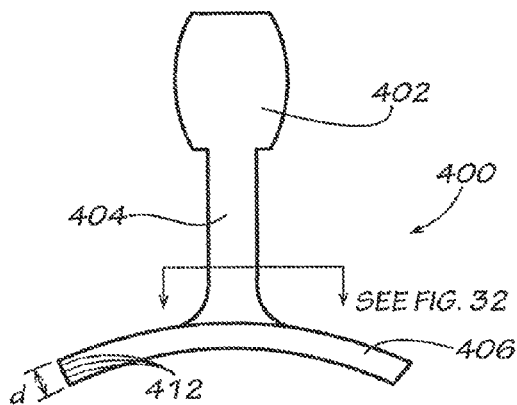
FIG. 31 is a view of a guide marker for an acetabular implant.
Figure 32:
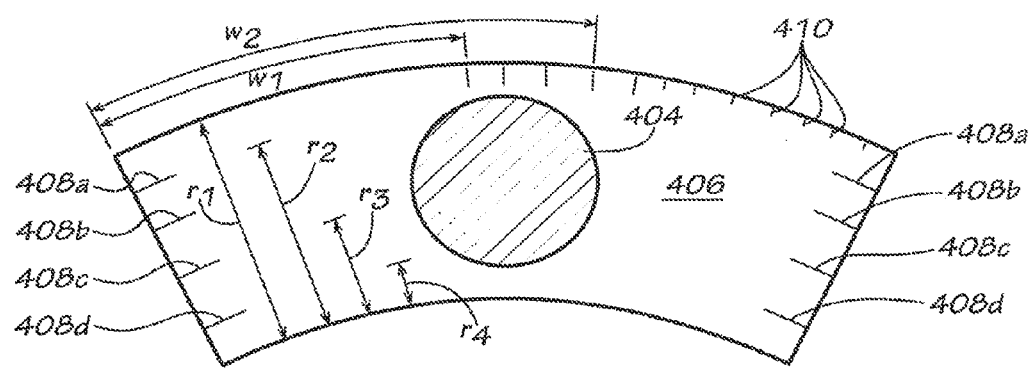
FIG. 32 is another view of the guide marker of FIG. 31.

FIG. 31 is a view of a guide marker 400 for an acetabular implant. A handle 402 extends along a shaft 404 to a guide 406. Depth indicia 412 on the guide 406 may set the depth of the implant while radii (r1, r2, r3, and r4) by markings 408 a-d (shown in FIG. 32). Widths (w1, w2) may be determined through markings 410. Based upon the necessary bone removal, the markings may determine the size of the implant, the depth to which the bone must be removed in order for the implant to fit properly, and the correct radius of the implant.

Figure 33:
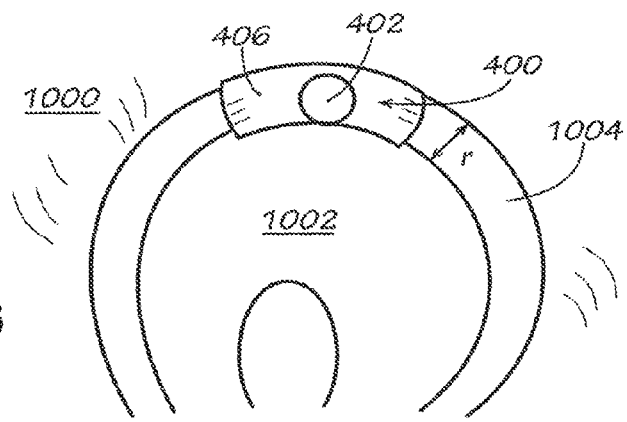
FIG. 33 is a view of the guide marker of FIG. 31 placed on the surface of an acetabulum.

FIG. 33 is a view of the guide marker of FIG. 31 placed on the surface of an acetabulum. The guide uses the radius markings to make sure the proper radius of the acetabulum is determined. By aligning an edge of the guide on one end of the damaged site, the width markings may be used to measure the width of the implant. The depth may be determined from the markings 112 which may show the depth of removal necessary for the implant to sit flush with the articulating surface of the acetabulum.

Figure 34:
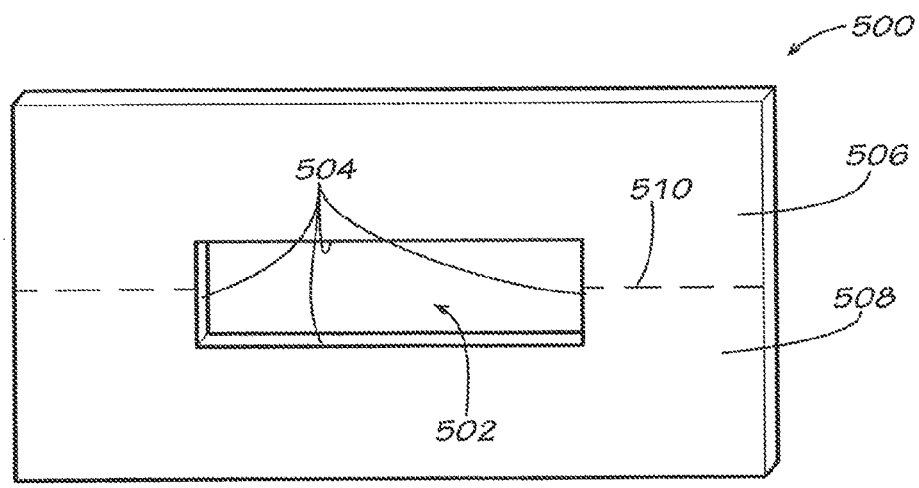
FIG. 34 is a view of a bone cutting guide.
Figure 35:
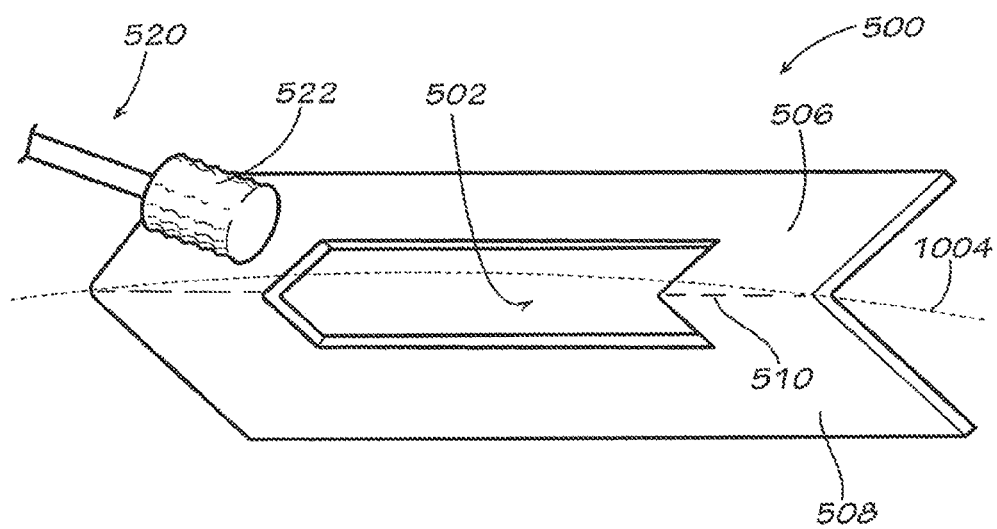
FIG. 35 is a view of a cutter and the bone cutting guide of FIG. 34 folded into a proper orientation to be received on an acetabulum.

FIG. 34 is a view of a bone cutting guide 500. An opening 502 in the guide 500 creates guide surfaces 504 for the depth of cutting. The guide 500 may be bent so that a lower portion 508 and an upper portion 506 overlie the rim of the acetabulum. As shown in FIG. 35, FIG. 35 is a view of a cutter 522 on a surgical tool 520 and the bone cutting guide of FIG. 34 folded into a proper orientation to be received on an acetabulum.

Figure 36:
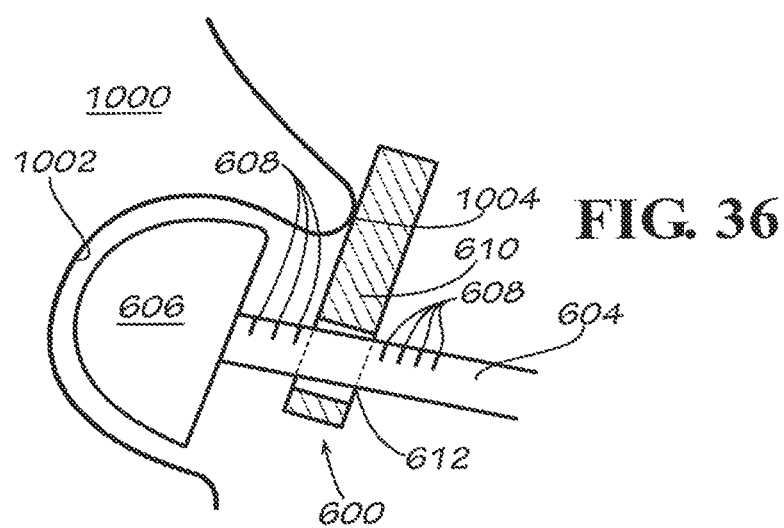
FIG. 36 is a view of a measuring instrument oriented in the acetabulum.
Figure 37:
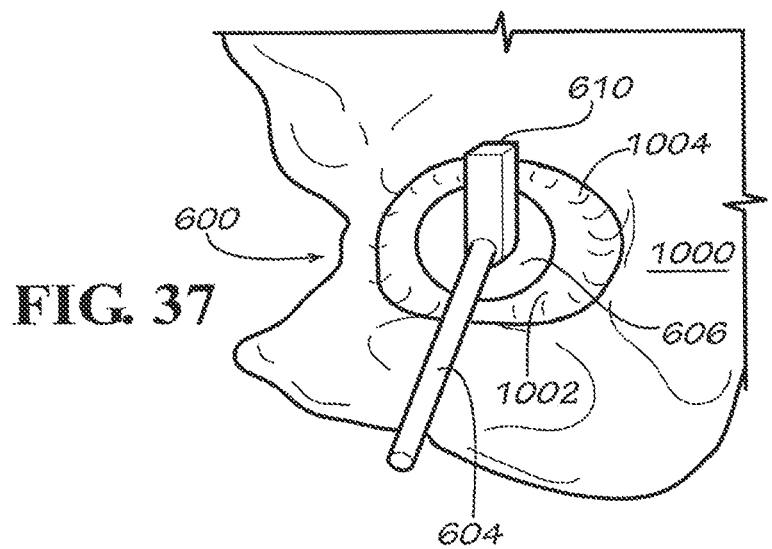
FIG. 37 is another view of the measuring instrument of FIG. 36 oriented in the acetabulum.

FIG. 36 is a view of a measuring instrument 600 oriented in the acetabulum 1002. The instrument 600 includes a shaft 604 attached to a hemispherical head 606. Depth marks 608 are located on the shaft 604. A stylus 610 slides along the shaft 604 in a shaft guide 612. The head 606 may be positioned within the acetabulum to orient the version and adduction of the shaft. The stylus may then measure the depth to the lesion 1004 by using the markings 608. Radius markings on the stylus may measure the radius of the acetabular rim. FIG. 37 is another view of the measuring instrument of FIG. 36 oriented in the acetabulum.

Figure 38:
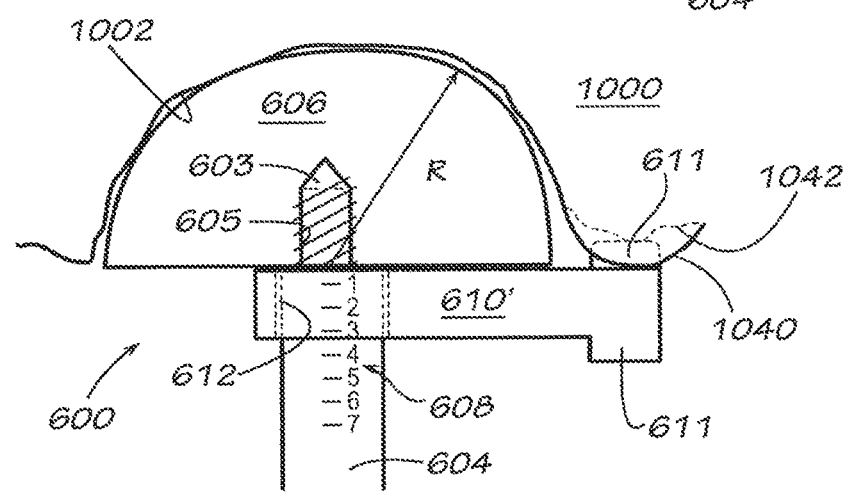
FIG. 38 is a view of another embodiment of a measuring instrument.

FIG. 38 is a view of another embodiment of a measuring instrument 600. The stylus 610' may be reversible. Additionally a lesion depth paddle 611 may be placed on the end of the stylus. The stylus 610' may measure the depth from the shaft, and the paddle 611 may measure the depth of the lesion.

Figure 39:
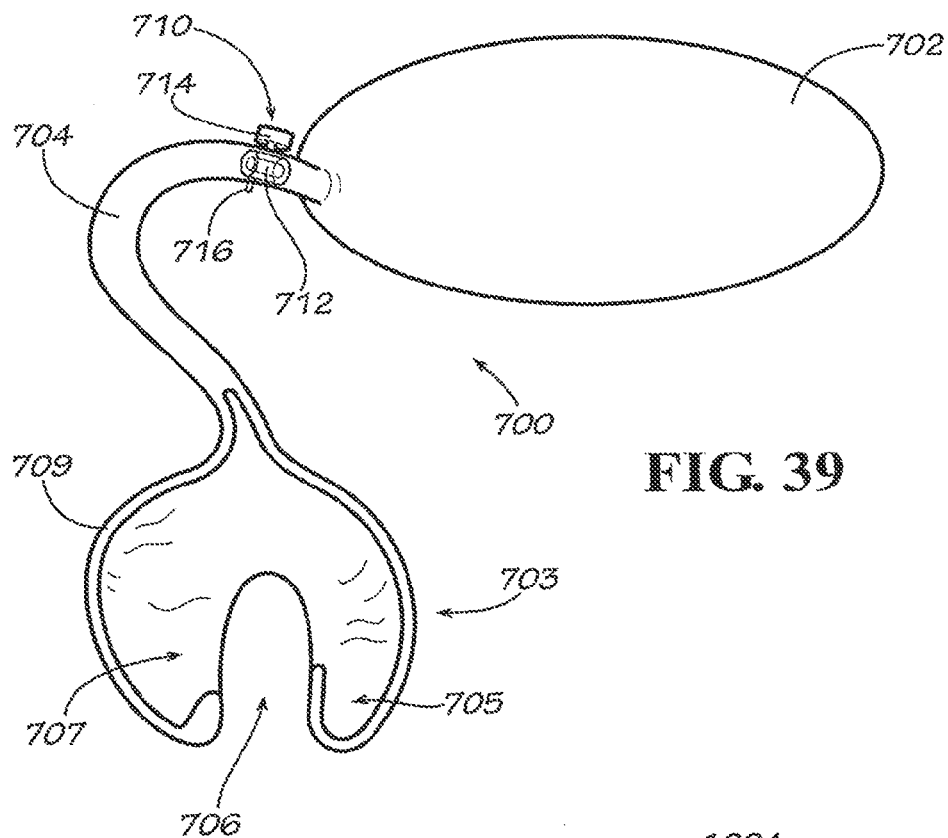
FIG. 39 is a view of a spacer instrument for separating the femur from the acetabulum.
Figure 40:
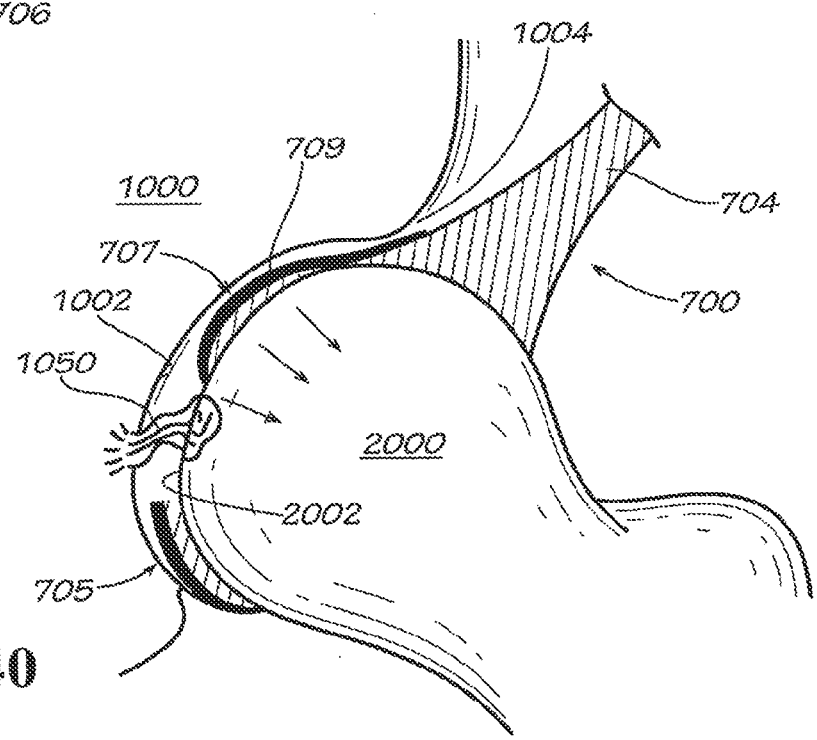
FIG. 40 is a partial view of the spacer instrument of FIG. 39 inserted into the hip joint around the ligamentum teres.

FIG. 39 is a view of a spacer instrument 700 for separating the femur from the acetabulum. The spacer instrument 700 includes a plenum 702 attached to a forked inflatable spoon 703 through a tube 704. The spoon 703 includes a first finger 705 and a second finger 707 separated by a cutout portion 706. A stiffening member 709 may stiffen the spoon 703 for insertion. A control module 710 includes a one way valve 712, a pressure release knob 714 and a pop-off valve 716. The plenum 702 may inflate the spoon 703 to inflate the finger portions 705 and 707. The finger portions 705 and 707 (as shown in FIG. 40) may avoid the ligamentum teres. When inflated, the spoon may separate the femur from the acetabulum without tearing the ligamentum teres. Stiffening means 709 may be placed along the edge of the spoon 703 so that the spoon may be pushed into the hip joint.

Figure 41:
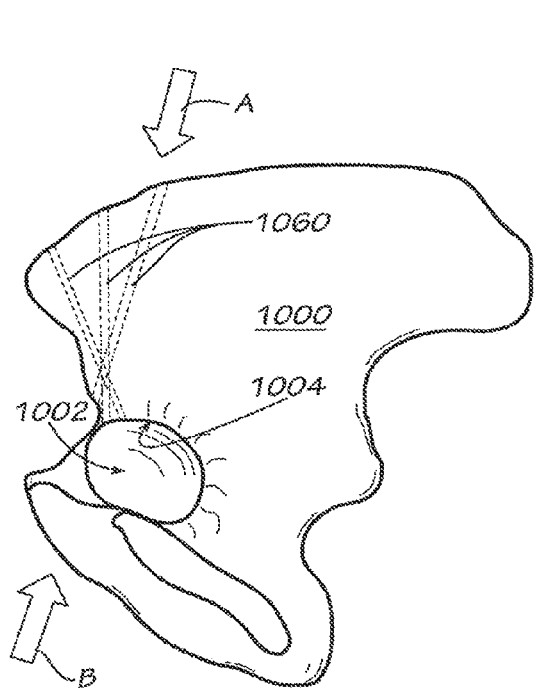
FIG. 41 is a view of an acetabulum showing pathways from the iliac crest to labral or acetabular defects.
Figure 42:
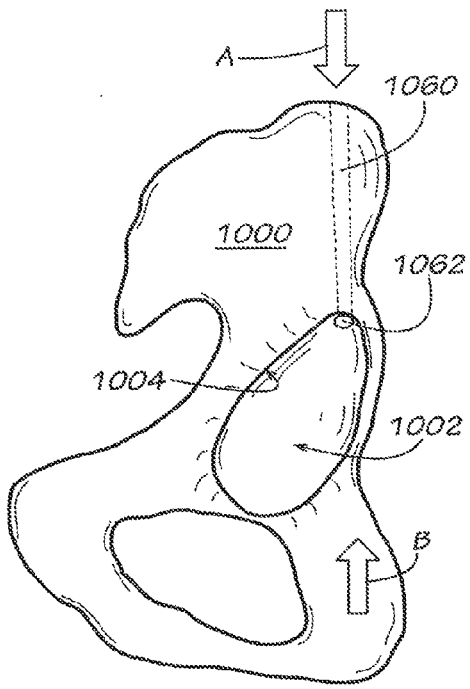
FIG. 42 is another view of the acetabulum of FIG. 41 showing pathways from the iliac crest to labral or acetabular defects.
Figures 43A, 43B, 43C, 43D, 43E, 43F:
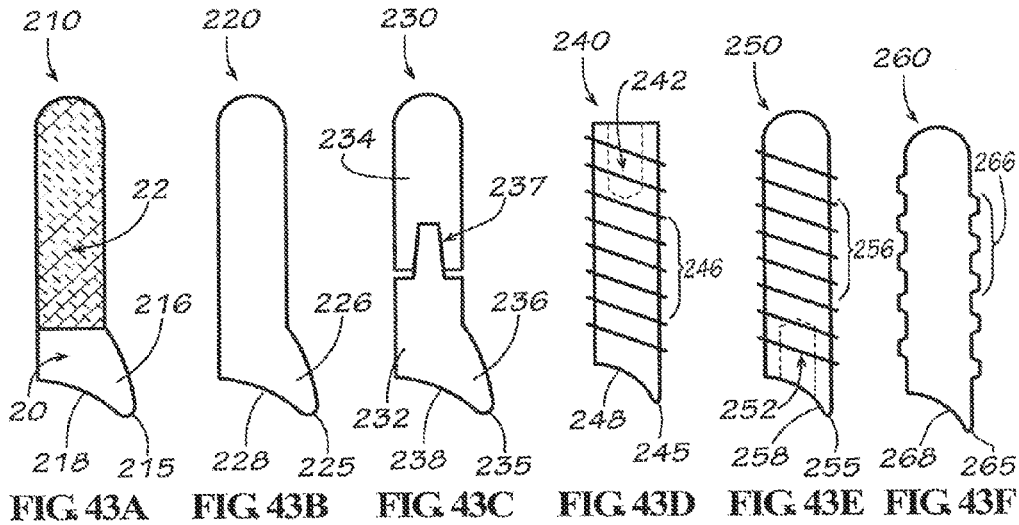
FIGS. 43A to 43F are views of different embodiments of acetabular implants to insert into the pathways shown in FIG. 41 and FIG. 42.

FIG. 41 is a view of an acetabulum showing pathways 1060 from the iliac crest to labral or acetabular defects. FIG. 42 is another view of the acetabulum of FIG. 41 showing pathways from the iliac crest to labral or acetabular defects. The pathways 1060 allow for distal to proximal orientation of an implant or a proximal to distal orientation of an implant. By using these different pathways through the iliac crest, the implant orientation at the labrum may be controlled. The implants inserted through these pathways are shown in FIGs. 43A to 43F.

FIGS. 43A to 43F are views of different embodiments of acetabular implants to insert into the pathways shown in FIG. 41 and FIG. 42. Each implant 210, 220, 230, 240, 250, and 260 have a post that extends along the pathway. Each implant has a ridge (like 215 in 43A), a bearing portion (e.g., 228 in FIG. 43B), and a rim portion (like 236 in FIG. 43C). The posts may be made of a compliant material 22, press fit into an implant, or threaded. Threaded designs may have rotational members 242 or 252 depending on proximal or distal direction of the implantation. The posts provide fixation for the implant in the bone 1000.

Figure 44:
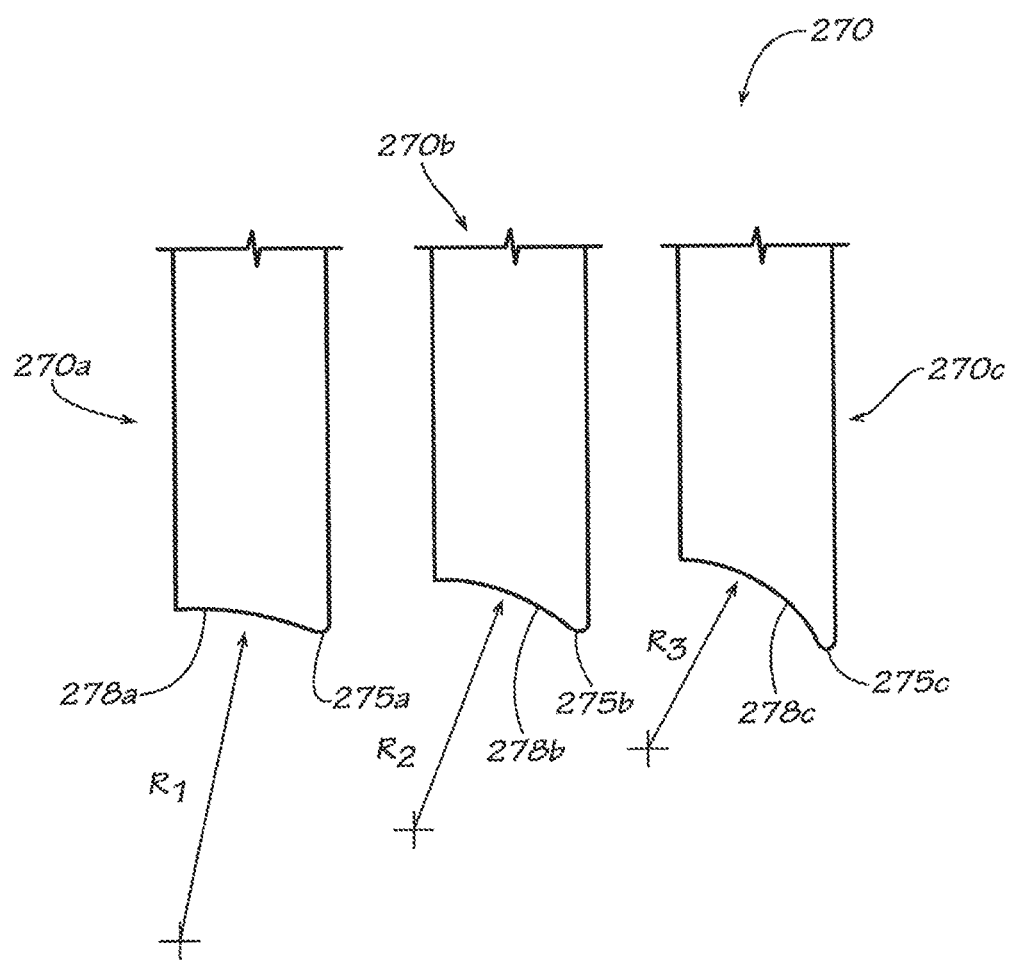
FIG. 44 is a view of a plurality of bone mating surfaces of acetabular implants having various radii.

FIG. 44 is a view of a plurality of bone mating surfaces 278a, 278b, and 278c of acetabular implants having various radii R1, R2, R3. With the varying radii and the varying directions, as well as the ability to control the depth of the implants in the bone, the proper orientation may be accomplished with good fixation, proper bearing placement and proper labrum replacement.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A partial rim implant for an acetabulum in a pelvic bone, wherein the acetabulum comprises an articulating surface, a rim, and an apex, the implant comprising:
    a ridge configured to replace a labrum of the acetabulum;
    a bearing surface configured to generally align with the articulating surface of the acetabulum, wherein the bearing surface extends from the ridge toward the apex of the acetabulum;
    an insertion portion extending away from the bearing surface and adapted to engage a recess in the pelvic bone; and
    at least one fixation flange extending from the ridge and away from the bearing surface, wherein the at least one fixation flange is configured for fixation to the pelvic bone to attach the implant to the pelvic bone with the bearing surface of the implant generally aligned with the articulating surface of the acetabulum and the ridge oriented to replace the labrum.

2. The implant of claim 1, wherein the at least one fixation flange defines at least one fastener opening for receiving a fastener sized and configured to extend into the pelvic bone to attach the implant to the pelvic bone.

3. The implant of claim 2, wherein the at least one fixation flange defines a plurality of the at least one fastener opening; and
    wherein a corresponding one of a plurality of fasteners is positioned within each of the plurality of the at least one fastener opening.

4. The implant of claim 1, wherein the bearing surface extends between the ridge and the insertion portion.

5. The implant of claim 4, wherein the bearing surface is curved between the ridge and the insertion portion.

6. The implant of claim 5, wherein the bearing surface comprises a concave curvature extending between the ridge and the insertion portion.

7. The implant of claim 1, wherein the insertion portion and the at least one fixation flange each extend away from the bearing surface in the same general direction and define a space therebetween sized and configured for receipt of a portion of the pelvic bone therein.

8. The implant of claim 1, wherein the at least one fixation flange comprises at least two fixation flanges extending from the ridge and away from the bearing surface, and wherein each of the at least two fixation flanges defines at least one fastener opening for receiving a fastener sized and configured to extend into the pelvic bone to attach the implant to the pelvic bone.

9. The implant of claim 1, further comprising at least one fastener opening extending through the ridge; and
 a fastener positioned within the at least one fastener opening and sized and configured to extend into the pelvic bone to attach the implant to the pelvic bone.

10. The implant of claim 1, wherein the insertion portion and the at least one fixation flange are angled toward one another as the insertion portion and the at least one fixation flange extend away from the bearing surface.

11. A partial rim implant for an acetabulum in a pelvic bone, wherein the acetabulum comprises an articulating surface, a rim, and an apex, the implant comprising:
 a ridge configured to replace a labrum of the acetabulum;
 a bearing surface configured to generally align with the articulating surface of the acetabulum, wherein the bearing surface extends from the ridge toward the apex of the acetabulum;
 an insertion portion extending away from the bearing surface and adapted to engage a recess in the pelvic bone;
 at least one fixation flange extending from the ridge and away from the bearing surface, wherein the at least one fixation flange defines at least one fastener opening; and
 a fastener positioned within each of the at least one fastener opening and sized and configured to extend into the pelvic bone to attach the implant to the pelvic bone with the bearing surface of the implant generally aligned with the articulating surface of the acetabulum and the ridge oriented to replace the labrum.

12. The implant of claim 11, wherein the at least one fixation flange is adapted to lie substantially flush with an outer surface of the pelvic bone.

13. The implant of claim 11, wherein the bearing surface extends between the ridge and the insertion portion.

14. The implant of claim 13, wherein the bearing surface is curved between the ridge and the insertion portion.

15. The implant of claim 14, wherein the bearing surface comprises a concave curvature extending between the ridge and the insertion portion.

16. The implant of claim 11, wherein the insertion portion and the at least one fixation flange each extend away from the bearing surface in the same general direction and define a space therebetween sized and configured for receipt of a portion of the pelvic bone therein.

17. The implant of claim 11, wherein the at least one fixation flange comprises at least two fixation flanges extending from the ridge and away from the bearing surface, and wherein each of the at least two fixation flanges defines the at least one of the fastener opening that receives a corresponding one of the fastener.

18. The implant of claim 11, wherein the at least one fixation flange defines a plurality of the at least one fastener opening; and
 wherein a corresponding one of a plurality of the fasteners is positioned within each of the plurality of the at least one fastener opening.

19. The implant of claim 11, further comprising at least one screw hole extending through the ridge; and
 a bone screw positioned within the at least one screw hole and sized and configured to extend into the pelvic bone to further secure the implant to the pelvic bone.

20. The implant of claim 11, wherein the insertion portion and the at least one fixation flange are angled toward one another as the insertion portion and the at least one fixation flange extend away from the bearing surface.

* * * * *